US012250870B2

United States Patent
Sasada et al.

(10) Patent No.: US 12,250,870 B2
(45) Date of Patent: Mar. 11, 2025

(54) LIGHT EMITTING DEVICE AND PRODUCTION METHOD THEREOF, AND COMPOSITION FOR LIGHT EMITTING DEVICE AND PRODUCTION METHOD THEREOF

(71) Applicant: Sumitomo Chemical Company, Limited, Tokyo (JP)

(72) Inventors: Toshiaki Sasada, Tsukuba (JP); Ryuji Matsumoto, Nomi (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 789 days.

(21) Appl. No.: 17/442,587

(22) PCT Filed: Mar. 16, 2020

(86) PCT No.: PCT/JP2020/011386
§ 371 (c)(1),
(2) Date: Sep. 23, 2021

(87) PCT Pub. No.: WO2020/203212
PCT Pub. Date: Oct. 8, 2020

(65) Prior Publication Data
US 2022/0190248 A1 Jun. 16, 2022

(30) Foreign Application Priority Data
Mar. 29, 2019 (JP) .................................. 2019-066199

(51) Int. Cl.
| | | |
|---|---|---|
| *H01L 51/50* | (2006.01) | |
| *C07C 15/28* | (2006.01) | |
| *C07D 409/14* | (2006.01) | |
| *C07F 5/02* | (2006.01) | |
| *C09K 11/06* | (2006.01) | |
| *H10K 85/30* | (2023.01) | |
| *H10K 85/60* | (2023.01) | |
| *H10K 50/12* | (2023.01) | |

(52) U.S. Cl.
CPC .......... *H10K 85/322* (2023.02); *C07C 15/28* (2013.01); *C07D 409/14* (2013.01); *C07F 5/027* (2013.01); *C09K 11/06* (2013.01); *H10K 85/626* (2023.02); *H10K 85/6572* (2023.02); *H10K 85/6576* (2023.02); *C07C 2603/24* (2017.05); *C09K 2211/1007* (2013.01); *C09K 2211/1011* (2013.01); *C09K 2211/1018* (2013.01); *H10K 50/121* (2023.02)

(58) Field of Classification Search
None
See application file for complete search history.

(56) References Cited

U.S. PATENT DOCUMENTS

| | | |
|---|---|---|
| 2012/0309974 A1 | 12/2012 | Cai et al. |
| 2019/0058124 A1* | 2/2019 | Hatakeyama ........ H10K 85/658 |
| 2019/0214569 A1 | 7/2019 | Sasada et al. |
| 2020/0176680 A1 | 6/2020 | Hatakeyama et al. |
| 2021/0135142 A1 | 5/2021 | Li et al. |
| 2021/0167288 A1 | 6/2021 | Hatakeyama et al. |
| 2021/0175454 A1* | 6/2021 | Sasada .................. H10K 71/70 |

FOREIGN PATENT DOCUMENTS

| | | |
|---|---|---|
| CN | 108610357 A | 10/2018 |
| CN | 110838549 A | 2/2020 |
| EP | 3109253 A1 | 12/2016 |
| JP | 2017126606 A | 7/2017 |
| WO | 2011098030 A1 | 8/2011 |
| WO | 2011099331 A1 | 8/2011 |
| WO | 2014102543 A2 | 7/2014 |
| WO | 2015102118 A1 | 7/2015 |
| WO | 2018062278 A1 | 4/2018 |
| WO | 2019009052 A1 | 1/2019 |
| WO | 2019035268 A1 | 2/2019 |
| WO | 2020045681 A1 | 3/2020 |

OTHER PUBLICATIONS

Extended European Search Report issued Oct. 18, 2022 in EP Application No. 20784855.7.
International Preliminary Report on Patentability issued Oct. 14, 2021 in International Application No. PCT/JP2020/011386.
International Search Report issued Jun. 30, 2020 in International Application No. PCT/JP2020/011386.
Office Action issued Mar. 2, 2021 in JP Application No. 2020031741.
Written Opinion issued Jun. 30, 2020 in International Application No. PCT/JP2020/011386.
Office Action and Search Report issued Jun. 7, 2023 in TW Application No. 109109805 (English translation).

(Continued)

*Primary Examiner* — Gregory D Clark
(74) *Attorney, Agent, or Firm* — Panitch Schwarze Belisario & Nadel LLP

(57) ABSTRACT

A light emitting device including an anode, a cathode, and an organic layer disposed between the anode and the cathode and containing a composition is provided. The composition contains two or more compounds (B) having a condensed hetero ring skeleton (b) containing a boron atom and a nitrogen atom in the ring. Compound (B) contains a compound (B1) and a compound (B2) which satisfy at least one of the following formulas: EB1<EB2 and AB1<AB2. EB1 represents the maximum peak wavelength of the emission spectrum at 25° C. of compound (B1), EB2 represents the maximum peak wavelength of the emission spectrum at 25° C. of compound (B2), AB1 represents the peak wavelength at the lowest energy side of the absorption spectrum at 25° C. of compound (B1), and AB2 represents the peak wavelength at the lowest energy side of the absorption spectrum at 25° C. of compound (B2).

23 Claims, No Drawings

(56) References Cited

OTHER PUBLICATIONS

Office Action issued Jun. 18, 2024 in CN Application No. 202080025159.2, with English machine translation.
Office Action issued Jun. 19, 2024 in KR Application No. 10-2021-7034270, with English machine translation.

* cited by examiner

LIGHT EMITTING DEVICE AND PRODUCTION METHOD THEREOF, AND COMPOSITION FOR LIGHT EMITTING DEVICE AND PRODUCTION METHOD THEREOF

CROSS-REFERENCE TO RELATED APPLICATIONS

This application is a Section 371 of International Application No. PCT/JP2020/011386, filed Mar. 16, 2020, which was published in the Japanese language on Oct. 8, 2020, under International Publication No. WO 2020/203212 A1, which claims priority under 35 U.S.C. § 119(b) to Japanese Application No. 2019-066199, filed Mar. 29, 2019, the disclosure of each of which is incorporated herein by reference in its entirety.

TECHNICAL FIELD

The present invention relates to a light emitting device and a production method thereof. Further, the present invention relates to a composition for light emitting device and a production method thereof.

BACKGROUND ART

Light emitting devices such as an organic electroluminescent device and the like can be suitably used, for example, for display and illumination. As the light emitting material used for a light emitting layer of a light emitting device, for example, Patent Document 1 suggests a composition containing a compound H1 and a compound G1.

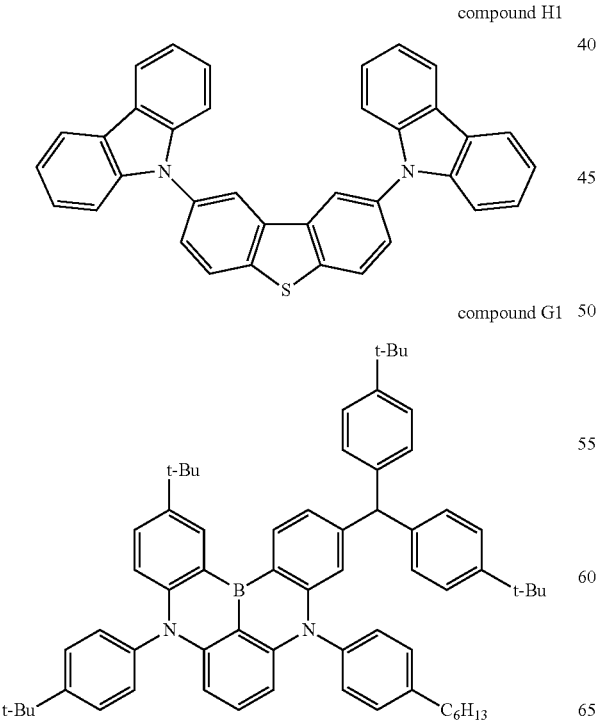

compound H1 compound G1

PRIOR ART DOCUMENT

Patent Document

[Patent Document 1] International Publication WO2018/062278

SUMMARY OF THE INVENTION

Problem to be Solved by the Invention

However, the light emitting device fabricated using the above-described composition was not necessarily sufficient in external quantum efficiency.

Then, the present invention has an object of providing a composition which is useful for producing a light emitting device excellent in external quantum efficiency, and a light emitting device containing the composition.

Means for Solving the Problem

The present inventors have intensively studied to solve the above-described problem and resultantly found that a light emitting device excellent in external quantum efficiency is formed with a composition for light emitting device containing two or more compounds (B) satisfying a specific relation, leading to completion of the present invention.

That is, the present invention provides the following [1] to [23].

[1] A light emitting device comprising
an anode,
a cathode, and
an organic layer disposed between the above-described anode and the above-described cathode and containing a composition for light emitting device,
wherein
the above-described composition for light emitting device contains two or more compounds (B) having a condensed hetero ring skeleton (b) containing a boron atom and a nitrogen atom in the ring, and
the above-described compound (B) contains a compound (B1) and a compound (B2) satisfying at least one of the formula (M-1) and the formula (M-2):

$$EB1 < EB2 \quad (M\text{-}1)$$

$$AB1 < AB2 \quad (M\text{-}2)$$

[wherein, EB1 represents the maximum peak wavelength [nm] of the emission spectrum at 25° C. of the compound (B1), EB2 represents the maximum peak wavelength [nm] of the emission spectrum at 25° C. of the compound (B2), AB1 represents the peak wavelength [nm] at the lowest energy side of the absorption spectrum at 25° C. of the compound (B1), and AB2 represents the peak wavelength [nm] at the lowest energy side of the absorption spectrum at 25° C. of the compound (B2).].

[2] The light emitting device according to [1], wherein at least one of the above-described compound (B1) and the above-described compound (B2) is a compound represented by the formula (1-1), a compound represented by the formula (1-2) or a compound represented by the formula (1-3):

[Chemical Formula 2]

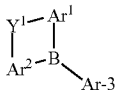

(1-1)

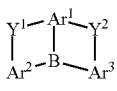

(1-2)

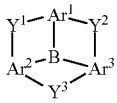

(1-3)

[wherein, $Ar^1$, $Ar^2$ and $Ar^3$ each independently represent an aromatic hydrocarbon group or a hetero ring group, and these groups optionally have a substituent. When a plurality of the substituents are present, they may be the same or different and may be combined together to form a ring together with atoms to which they are attached.

$Y^1$ represents a group represented by —N(Ry)-.

$Y^2$ and $Y^3$ each independently represent a single bond, an oxygen atom, a sulfur atom, a selenium atom, a group represented by —N(Ry)-, an alkylene group or a cycloalkylene group, and these groups optionally have a substituent. When a plurality of the substituents are present, they may be the same or different and may be combined together to form a ring together with atoms to which they are attached. Ry represents a hydrogen atom, an alkyl group, a cycloalkyl group, an aryl group or a monovalent hetero ring group, and these groups optionally have a substituent. When a plurality of the substituents are present, they may be the same or different and may be combined together to form a ring together with atoms to which they are attached. When a plurality of Ry are present, they may be the same or different. Ry may be bonded directly or via a connecting group to $Ar^1$, $Ar^2$ or $Ar^3$.].

[3] The light emitting device according to [2], wherein both the above-described compound (B1) and the above-described compound (B2) represent the above-described compound represented by the formula (1-1), the above-described compound represented by the formula (1-2) or the above-described compound represented by the formula (1-3).

[4] The light emitting device according to [2] or [3], wherein at least one of the above-described compound (B1) and the above-described compound (B2) is the above-described compound represented by the formula (1-2).

[5] The light emitting device according to [4], wherein both the above-described compound (B1) and the above-described compound (B2) represent the above-described compound represented by the formula (1-2).

[6] The light emitting device according to any one of [2] to [5], wherein the above-described $Y^2$ and the above-described $Y^3$ are groups represented by —N(Ry)-.

[7] The light emitting device according to any one of [1] to [6], wherein the above-described compound (B1) and the above-described compound (B2) satisfy the above-described formula (M-2).

[8] The light emitting device according to any one of [1] to [7], wherein at least one of the absolute value of a difference between the above-described EB1 and the above-described AB2 and the absolute value of a difference between the above-described EB2 and the above-described AB1 is 200 nm or less.

[9] The light emitting device according to any one of [1] to [8], wherein the absolute value of a difference between the energy level of the lowest triplet excited state and the energy level of the lowest singlet excited state of the above-described compound (B1) is 0.50 eV or less, and the absolute value of a difference between the energy level of the lowest triplet excited state and the energy level of the lowest singlet excited state of the above-described compound (B2) is 0.50 eV or less.

[10] The light emitting device according to any one of [1] to [9], wherein the above-described composition for light emitting device further contains a host material.

[11] The light emitting device according to [10], wherein the above-described host material contains a compound represented by the formula (H-1):

[Chemical Formula 3]

(H-1)

[wherein, $Ar^{H1}$ and $Ar^{H2}$ each independently represent an aryl group, a monovalent hetero ring group or a substituted amino group, and these groups optionally have a substituent. When a plurality of the substituents are present, they may be the same or different and may be combined together to form a ring together with atoms to which they are attached.

$n^{H1}$ represents an integer of 0 or more.

$L^{H1}$ represents an arylene group, a divalent hetero ring group, an alkylene group or a cycloalkylene group, and these groups optionally have a substituent. When a plurality of the substituents are present, they may be the same or different and may be combined together to form a ring together with atoms to which they are attached. When a plurality of $L^{H1}$ are present, they may be the same or different.].

[12] The light emitting device according to [10] or [11], wherein the difference between the maximum peak wavelength EH [nm] of the emission spectrum at 25° C. of the above-described host material and at least one of the above-described AB1 and the above-described AB2 is 200 nm or less.

[13] The light emitting device according to any one of [1] to [12], wherein the above-described composition for light emitting device further contains at least one selected from the group consisting of a hole transporting material, a hole injection material, an electron transporting material, an electron injection material, a light emitting material, an antioxidant and a solvent.

[14] A composition for light emitting device comprising two or more compounds (B) having a condensed hetero ring skeleton (b) containing a boron atom and a nitrogen atom in the ring, wherein the above-described compound (B) contains a compound (B1) and a compound (B2) satisfying at least one of the formula (M-1) and the formula (M-2):

$$EB1 < EB2 \quad (M\text{-}1)$$

$$AB1 < AB2 \quad (M\text{-}2)$$

[wherein, EB1 represents the maximum peak wavelength [nm] of the emission spectrum at 25° C. of the compound (B1), EB2 represents the maximum peak wavelength [nm] of the emission spectrum at 25° C. of the compound (B2), AB1 represents the peak wavelength [nm] at the lowest energy side of the absorption spectrum at 25° C. of the compound (B1), and AB2 represents the peak wavelength [nm] at the lowest energy side of the absorption spectrum at 25° C. of the compound (B2).].

[15] The composition for light emitting device according to [14], further comprising a host material.

[16] The composition for light emitting device according to [15], wherein the above-described host material contains a compound represented by the formula (H-1):

[Chemical Formula 4]

(H-1)

[wherein,
Ar$^{H1}$ and Ar$^{H2}$ each independently represent an aryl group, a monovalent hetero ring group or a substituted amino group, and these groups optionally have a substituent. When a plurality of the substituents are present, they may be the same or different and may be combined together to form a ring together with atoms to which they are attached.

n$^{H1}$ represents an integer of 0 or more.

L$^{H1}$ represents an arylene group, a divalent hetero ring group, an alkylene group or a cycloalkylene group, and these groups optionally have a substituent. When a plurality of the substituents are present, they may be the same or different and may be combined together to form a ring together with atoms to which they are attached. When a plurality of L$^{H1}$ are present, they may be the same or different.].

[17] The composition for light emitting device according to [15] or [16], wherein the difference between the maximum peak wavelength EH [nm] of the emission spectrum at 25° C. of the above-described host material and at least one of the above-described AB1 and the above-described AB2 is 200 nm or less.

[18] The composition for light emitting device according to any one of [14] to [17], further comprising at least one selected from the group consisting of a hole transporting material, a hole injection material, an electron transporting material, an electron injection material, a light emitting material, an antioxidant and a solvent.

[19] A method for producing a composition for light emitting device, comprising
a preparation step of preparing a compound (B1) having a condensed hetero ring skeleton (b1) containing a boron atom and a nitrogen atom in the ring,
a sorting step of sorting a compound (B2) having a condensed hetero ring skeleton (b2) containing a boron atom and a nitrogen atom in the ring and in which the maximum peak wavelength of the emission spectrum at 25° C. is larger than the maximum peak wavelength of the emission spectrum at 25° C. of the above-described compound (B1) and/or the peak wavelength at the lowest energy side of the absorption spectrum at 25° C. is smaller than the peak wavelength at the lowest energy side of the absorption spectrum at 25° C. of the above-described compound (B1), and
a production step of mixing the compound (B1) prepared in the above-described preparation step and the compound (B2) sorted in the above-described sorting step to obtain a composition for light emitting device.

[20] The production method according to [19], wherein the above-described sorting step includes a step of determining the maximum peak wavelength of the emission spectrum at 25° C. of the above-described compound (B2) and/or the peak wavelength at the lowest energy side of the absorption spectrum at 25° C. of the above-described compound (B2).

[21] A method for producing a composition for light emitting device, comprising
a preparation step of preparing a compound (B2) having a condensed hetero ring skeleton (b2) containing a boron atom and a nitrogen atom in the ring,
a sorting step of sorting a compound (B1) having a condensed hetero ring skeleton (b1) containing a boron atom and a nitrogen atom in the ring and in which the maximum peak wavelength of the emission spectrum at 25° C. is smaller than the maximum peak wavelength of the emission spectrum at 25° C. of the above-described compound (B2) and/or the peak wavelength at the lowest energy side of the absorption spectrum at 25° C. is larger than the peak wavelength at the lowest energy side of the absorption spectrum at 25° C. of the above-described compound (B2), and
a production step of mixing the compound (B2) prepared in the above-described preparation step and the compound (B1) sorted in the above-described sorting step to obtain a composition for light emitting device.

[22] The production method according to [21], wherein the above-described sorting step includes a step of determining the maximum peak wavelength of the emission spectrum at 25° C. of the above-described compound (B1) and/or the peak wavelength at the lowest energy side of the absorption spectrum at 25° C. of the above-described compound (B1).

[23] A method for producing a light emitting device having an anode, a cathode, and an organic layer disposed between the above-described anode and the above-described cathode, comprising
a step of producing a composition for light emitting device by the production method as described in any one of [19] to [22], and
a step of forming the above-described organic layer using the above-described composition for light emitting device produced in the above step.

Effect of the Invention

According to the present invention, it is possible to provide a composition which is useful for producing a light emitting device excellent in external quantum efficiency, and a production method thereof. Further, according to the present invention, it is possible to provide a light emitting device containing the composition, and a production method thereof.

MODES FOR CARRYING OUT THE INVENTION

Suitable embodiments of the present invention will be illustrated in detail below.

Explanation of Common Terms

Terms commonly used in the present specification have the following meanings unless otherwise stated.

"Room temperature" denotes 25° C.

Me represents a methyl group, Et represents an ethyl group, Bu represents a butyl group, i-Pr represents an isopropyl group, and t-Bu represents a tert-butyl group.

A hydrogen atom may be a heavy hydrogen atom or a light hydrogen atom.

"The low molecular weight compound" means a compound having no molecular weight distribution and having a molecular weight of $1 \times 10^4$ or less.

"The polymer compound" means a polymer having molecular weight distribution and having a polystyrene-equivalent number-average molecular weight of $1 \times 10^3$ or more (for example, $1 \times 10^3$ to $1 \times 10^8$).

"The constitutional unit" means a unit occurring once or more times in the polymer compound.

The polymer compound may be any of a block copolymer, a random copolymer, an alternating copolymer and a graft copolymer, and may also be another form.

The end group of the polymer compound is preferably a stable group since if a polymerization active group remains intact there, there is a possibility of a decrease in light emitting properties or luminance life when the polymer compound is used for fabrication of a light emitting device. The end group of the polymer compound is preferably a group conjugatively bonded to the main chain and includes, for example, groups bonding to an aryl group or a monovalent hetero ring group linking to the main chain of the polymer compound via a carbon-carbon bond.

"The alkyl group" may be any of linear and branched. The number of carbon atoms of the linear alkyl group, not including the number of carbon atoms of the substituent, is usually 1 to 50, preferably 1 to 20, and more preferably 1 to 10. The number of carbon atoms of the branched alkyl group, not including the number of carbon atoms of the substituent, is usually 3 to 50, preferably 3 to 20, and more preferably 4 to 10.

The alkyl group optionally has a substituent. The alkyl group includes, for example, a methyl group, an ethyl group, a propyl group, an isopropyl group, a butyl group, a 2-butyl group, an isobutyl group, a tert-butyl group, a pentyl group, an isoamyl group, a 2-ethylbutyl group, a hexyl group, a heptyl group, an octyl group, a 2-ethylhexyl group, a 3-propylheptyl group, a decyl group, a 3,7-dimethyloctyl group, a 2-ethyloctyl group, a 2-hexyldecyl group and a dodecyl group. Further, the alkyl group may also be a group obtained by substituting a part or all of hydrogen atoms in these groups with a cycloalkyl group, an alkoxy group, a cycloalkoxy group, an aryl group, a fluorine atom or the like. Such an alkyl group includes, for example, a trifluoromethyl group, a pentafluoroethyl group, a perfluorobutyl group, a perfluorohexyl group, a perfluorooctyl group, a 3-phenylpropyl group, a 3-(4-methylphenyl)propyl group, a 3-(3,5-di-hexylphenyl)propyl group and a 6-ethyloxyhexyl group.

The number of carbon atoms of "the cycloalkyl group", not including the number of carbon atoms of the substituent, is usually 3 to 50, and preferably 4 to 10. The cycloalkyl group optionally has a substituent. The cycloalkyl group includes, for example, a cyclohexyl group and a methylcyclohexyl group.

The number of carbon atoms of "the alkylene group", not including the number of carbon atoms of the substituent, is usually 1 to 20, preferably 1 to 15, and more preferably 1 to 10. The alkylene group optionally has a substituent. The alkylene group includes, for example, a methylene group, an ethylene group, a propylene group, a butylene group, a hexylene group and an octylene group.

The number of carbon atoms of "the cycloalkylene group", not including the number of carbon atoms of the substituent, is usually 3 to 20, and preferably 4 to 10. The cycloalkylene group optionally has a substituent. The cycloalkylene group includes, for example, a cyclohexylene group.

"The aromatic hydrocarbon group" means a group obtained by removing from an aromatic hydrocarbon one or more hydrogen atoms bonding directly to atoms constituting the ring. The group obtained by removing from an aromatic hydrocarbon one hydrogen atom bonding directly to an atom constituting the ring is referred to also as "aryl group". The group obtained by removing from an aromatic hydrocarbon two hydrogen atoms bonding directly to atoms constituting the ring is referred to also as "arylene group".

The number of carbon atoms of the aromatic hydrocarbon group, not including the number of carbon atoms of the substituent, is usually 6 to 60, preferably 6 to 40, and more preferably 6 to 20.

"The aromatic hydrocarbon group" includes, for example, groups obtained by removing from a monocyclic aromatic hydrocarbon (including, for example, benzene) or a polycyclic aromatic hydrocarbon (including, for example, dicyclic aromatic hydrocarbons such as naphthalene, indene and the like; tricyclic aromatic hydrocarbons such as anthracene, phenanthrene, dihydrophenanthrene, fluorene and the like; tetracyclic aromatic hydrocarbons such as benzoanthracene, benzophenanthrene, benzofluorene, pyrene, fluoranthene and the like; pentacyclic aromatic hydrocarbons such as dibenzoanthracene, dibenzophenanthrene, dibenzofluorene, perylene, benzofluoranthene and the like; hexacyclic aromatic hydrocarbons such as spirobifluorene and the like; and, heptacyclic aromatic hydrocarbons such as benzospirobifluorene, acenaphthofluoranthene and the like) one or more hydrogen atoms bonding directly to atoms constituting the ring. The aromatic hydrocarbon group includes groups obtained by bonding a plurality of these groups. The aromatic hydrocarbon group optionally has a substituent.

"The alkoxy group" may be any of linear and branched. The number of carbon atoms of the linear alkoxy group, not including the number of carbon atoms of the substituent, is usually 1 to 40, and preferably 1 to 10. The number of carbon atoms of the branched alkoxy group, not including the number of carbon atoms of the substituent, is usually 3 to 40, and preferably 4 to 10.

The alkoxy group optionally has a substituent. The alkoxy group includes, for example, a methoxy group, an ethoxy group, an isopropyloxy group, a butyloxy group, a hexyloxy group, a 2-ethylhexyloxy group, a 3,7-dimethyloctyloxy group and a lauryloxy group.

The number of carbon atoms of "the cycloalkoxy group", not including the number of carbon atoms of the substituent, is usually 3 to 40, and preferably 4 to 10. The cycloalkoxy group optionally has a substituent. The cycloalkoxy group includes, for example, a cyclohexyloxy group.

The number of carbon atoms of "the aryloxy group", not including the number of carbon atoms of the substituent, is usually 6 to 60, preferably 6 to 40, and more preferably 6 to 20. The aryloxy group optionally has a substituent. The aryloxy group includes, for example, a phenoxy group, a naphthyloxy group, an anthracenyloxy group and a pyrenyloxy group.

"The hetero ring group" means a group obtained by removing from a heterocyclic compound one or more hydrogen atoms bonding directly to atoms constituting the ring. Of the hetero ring groups, "an aromatic hetero ring group" which is a group obtained by removing from an aromatic heterocyclic compound one or more hydrogen atoms bonding directly to atoms constituting the ring is preferred. The group obtained by removing from a heterocyclic compound p hydrogen atoms (p represents an integer of 1 or more) bonding directly to atoms constituting the ring is referred to also as "p-valent hetero ring group". The group obtained by removing from an aromatic heterocyclic compound p hydrogen atoms bonding directly to atoms constituting the ring is referred to also as "p-valent aromatic hetero ring group".

"The aromatic heterocyclic compound" includes, for example, compounds in which the hetero ring itself shows aromaticity such as azole, thiophene, furan, pyridine, diazabenzene, triazine, azanaphthalene, diazanaphthalene, carbazole and the like, and compounds in which an aromatic ring is condensed to a hetero ring even if the hetero ring itself shows no aromaticity such as phenoxazine, phenothiazine, benzopyran and the like.

The number of carbon atoms of the hetero ring group, not including the number of carbon atoms of the substituent, is usually 1 to 60, preferably 2 to 40, and more preferably 3 to 20. The number of hetero atoms of the aromatic hetero ring group, not including the number of hetero atoms of the substituent, is usually 1 to 30, preferably 1 to 10, more preferably 1 to 5, and further preferably 1 to 3.

The hetero ring group includes, for example, groups obtained by removing from a monocyclic heterocyclic compound (including, for example, furan, thiophene, oxadiazole, pyrrole, diazole, triazole, tetrazole, pyridine, diazabenzene and triazine) or a polycyclic heterocyclic compound (including, for example, dicyclic heterocyclic compounds such as azanaphthalene, diazanaphthalene, benzofuran, benzothiophene, indole, benzodiazole, benzothiadiazole and the like; tricyclic heterocyclic compounds such as dibenzofuran, dibenzothiophene, dibenzoborole, dibenzosilole, dibenzophosphole, dibenzoselenophene, carbazole, azacarbazole, diazacarbazole, phenoxazine, phenothiazine, 9,10-dihydroacridine, 5,10-dihydrophenazine, phenazaborine, phenophosphazine, phenoselenazine, phenazasiline, azaanthracene, diazaanthracene, azaphenanthrene, diazaphenanthrene and the like; tetracyclic heterocyclic compounds such as hexaazatriphenylene, benzocarbazole, benzonaphthofuran, benzonaphthothiophene and the like; pentacyclic heterocyclic compounds such as dibenzocarbazole, indolocarbazole, indenocarbazole and the like; hexacyclic heterocyclic compounds such as carbazolocarbazole, benzoindolocarbazole, benzoindenocarbazole and the like; and, heptacyclic heterocyclic compounds such as dibenzoindolocarbazole and the like) one or more hydrogen atoms bonding directly to atoms constituting the ring. The hetero ring group includes groups obtained by bonding a plurality of these groups. The hetero ring group optionally has a substituent.

"The halogen atom" denotes a fluorine atom, a chlorine atom, a bromine atom or an iodine atom.

"The amino group" optionally has a substituent, and substituted amino groups (namely, secondary amino groups or tertiary amino groups, more preferably tertiary amino groups) are preferred. The substituent which the amino group has is preferably an alkyl group, a cycloalkyl group, an aryl group or a monovalent hetero ring group. When a plurality of the substituents which the amino group has are present, they may be the same or different and may be combined together to form a ring together with nitrogen atoms to which they are attached.

The substituted amino group includes, for example, a dialkylamino group, a dicycloalkylamino group and a diarylamino group.

The amino group includes, for example, a dimethylamino group, a diethylamino group, a diphenylamino group, a bis(methylphenyl)amino group and a bis(3,5-di-tert-butylphenyl)amino group.

"The alkenyl group" may be any of linear or branched. The number of carbon atoms of the linear alkenyl group, not including the number of carbon atoms of the substituent, is usually 2 to 30, and preferably 3 to 20. The number of carbon atoms of the branched alkenyl group, not including the number of carbon atoms of the substituent, is usually 3 to 30, and preferably 4 to 20.

The number of carbon atoms of "the cycloalkenyl group", not including the number of carbon atoms of the substituent, is usually 3 to 30, and preferably 4 to 20.

The alkenyl group and the cycloalkenyl group optionally have a substituent. The alkenyl group includes, for example, a vinyl group, a 1-propenyl group, a 2-butenyl group, a 3-butenyl group, a 3-pentenyl group, a 4-pentenyl group, a 1-hexenyl group, a 5-hexenyl group and a 7-octenyl group, and groups obtained by substituting a part or all of hydrogen atoms in these groups with a substituent. The cycloalkenyl group includes, for example, a cyclohexenyl group, a cyclohexadienyl group, a cyclooctatrienyl group and a norbornylenyl group, and groups obtained by substituting a part or all of hydrogen atoms in these groups with a substituent.

"The alkynyl group" may be any of linear or branched. The number of carbon atoms of the alkynyl group, not including carbon atoms of the substituent, is usually 2 to 20, and preferably 3 to 20. The number of carbon atoms of the branched alkynyl group, not including carbon atoms of the substituent, is usually 4 to 30, and preferably 4 to 20.

The number of carbon atoms of "the cycloalkynyl group", not including carbon atoms of the substituent, is usually 4 to 30, and preferably 4 to 20.

The alkynyl group and the cycloalkynyl group optionally have a substituent. The alkynyl group includes, for example, an ethynyl group, a 1-propynyl group, a 2-propynyl group, a 2-butynyl group, a 3-butynyl group, a 3-pentynyl group, a 4-pentynyl group, a 1-hexynyl group and a 5-hexynyl group, and groups obtained by substituting a part or all of hydrogen atoms in these groups with a substituent. The cycloalkynyl group includes, for example, a cyclooctynyl group.

"The cross-linkable group" refers to a group capable of generating a new bond by being subjected to a heating treatment, an ultraviolet irradiation treatment, a near-ultraviolet irradiation treatment, a visible light irradiation treatment, an infrared irradiation treatment, a radical reaction and the like. As the cross-linkable group, cross-linkable groups selected from Group A of cross-linkable group (namely, groups represented by any of the formula (XL-1) to the formula (XL-19)) are preferred.

(Group a of Cross-Linkable Group)

[Chemical Formula 5]

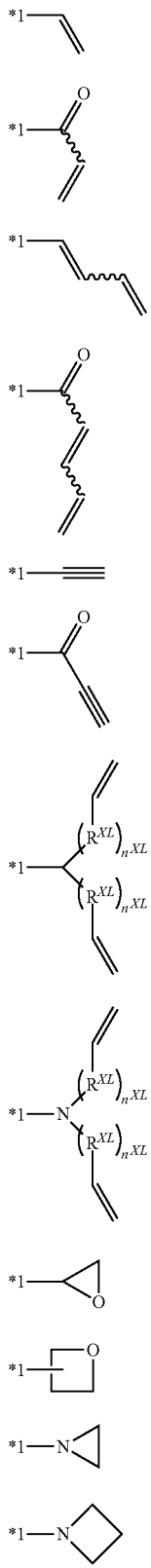

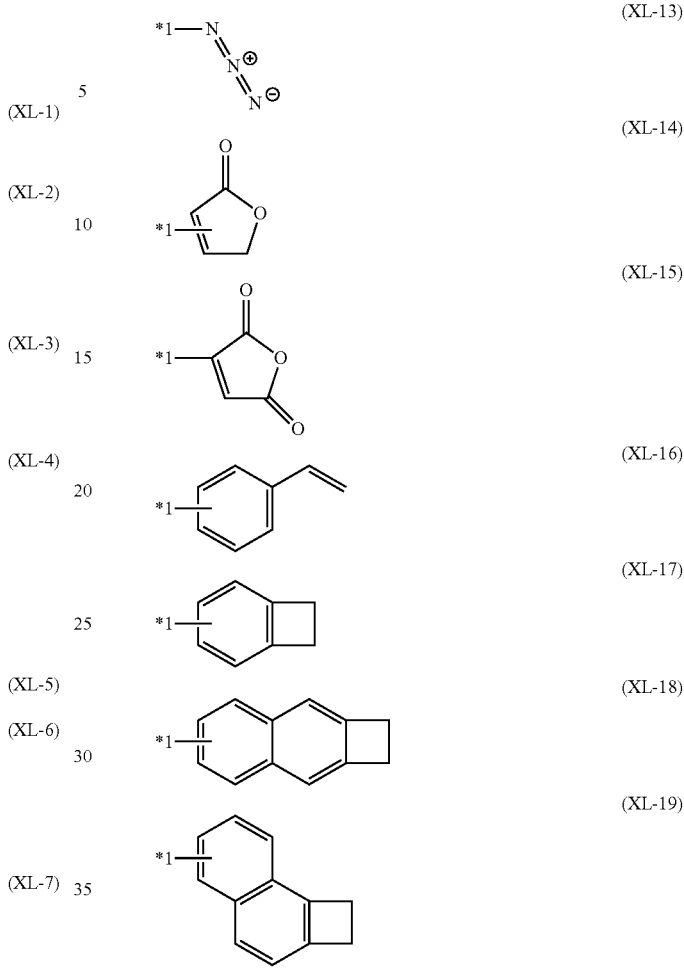

[wherein, $R^{XL}$ represents a methylene group, an oxygen atom or a sulfur atom, and $n^{XL}$ represents an integer of 0 to 5. When a plurality of $R^{XL}$ are present, they may be the same or different. A plurality of $n^{XL}$ may be the same or different. *1 represents a binding position. These cross-linkable groups optionally have a substituent. When a plurality of the substituents are present, they may be the same or different and may be combined together to form a ring together with carbon atoms to which they are attached.]

"The substituent" includes, for example, a halogen atom, a cyano group, an alkyl group, a cycloalkyl group, an aryl group, a monovalent hetero ring group, an alkoxy group, a cycloalkoxy group, an aryloxy group, an amino group, a substituted amino group, an alkenyl group, a cycloalkenyl group, an alkynyl group and a cycloalkynyl group. The substituent may be a cross-linkable group. When a plurality of the substituents are present, they may be combined together to form a ring together with atoms to which they are attached, but it is preferable that they do not form a ring.

In the present specification, calculation of the value of the absolute value of a difference between the energy level of the lowest triplet excited state and the energy level of the lowest singlet excited state (hereinafter, referred to also as "$\Delta E_{ST}$") is carried out by the following method. First, the ground state of a compound is structurally optimized by density-functional approach at B3LYP level. In this procedure, 6-31G* is used as the basis function. Using the resultant structurally optimized structure, $\Delta E_{ST}$ of the compound is calculated by B3LYP level time-dependent density-functional approach. In the case of containing an atom to which 6-31G* cannot be applied, LANL2DZ is used for the atom. Calculation is performed using Gaussian09, as the quantum chemistry calculation program.

<Composition for Light Emitting Device>

The composition for light emitting device of the present embodiment contains two or more compounds (B).

The composition for light emitting device of the present embodiment may contain only two kinds of the compound (B), or may contain three or more kinds thereof.

In the composition for light emitting device of the present embodiment, the content of at least one of the compounds (B) is usually 0.01 to 99.99 parts by mass, when the sum of the compounds (B) is taken as 100 parts by mass, and it is preferably 0.1 to 99.9 parts by mass, more preferably 1 to 99 parts by mass, further preferably 10 to 90 parts by mass, particularly preferably 20 to 80 parts by mass, and especially preferably 40 to 60 parts by mass, since the light emitting device of the present embodiment is more excellent in external quantum efficiency.

The composition for light emitting device according to the present embodiment may contain a compound (B1) and a compound (B2) as the compound (B).

In the composition for light emitting device of the present embodiment, the content of the compound (B1) is usually 0.01 to 99.99 parts by mass, when the sum of the compound (B1) and the compound (B2) is taken as 100 parts by mass, and it is preferably 0.1 to 99.9 parts by mass, more preferably 1 to 99 parts by mass, further preferably 10 to 90 parts by mass, particularly preferably 20 to 80 parts by mass, and especially preferably 40 to 60 parts by mass, since the light emitting device of the present embodiment is more excellent in external quantum efficiency.

In the composition for light emitting device of the present embodiment, the total content of the compound (B1) and the compound (B2) is usually 1 part by mass or more, when the sum of the compounds (B) is taken as 100 parts by mass, and it is preferably 10 parts by mass or more, more preferably 30 parts by mass or more, further preferably 50 parts by mass or more, particularly preferably 70 parts by mass or more, and especially preferably 90 parts by mass or more. Meanwhile, the total content of the compound (B1) and the compound (B2) may be 100 parts by mass, when the sum of the compounds (B) is taken as 100 parts by mass, and may also be below 100 parts by mass.

In the composition for light emitting device of the present embodiment, the compound (B1) and the compound (B2) preferably interact physically, chemically or electrically. By this interaction, it becomes possible to improve or adjust, for example, the light emitting properties, the charge transportability or the charge injectability of the composition for light emitting device of the present embodiment, and the light emitting device of the present embodiment is more excellent in external quantum efficiency.

In the composition for light emitting device of the present embodiment, when the compound (B1) and the compound (B2) satisfy at least one of the formula (M-1) and the formula (M-2), the compound (B1) and the compound (B2) efficiently interact physically, chemically or electrically, thus, the light emitting device of the present embodiment is more excellent in external quantum efficiency. In the composition for light emitting device of the present embodiment, it is preferable that the compound (B1) and the compound (B2) satisfy at least the formula (M-2), since the light emitting device of the present embodiment is more excellent in external quantum efficiency.

Under the above-mentioned conditions, the relationship between the formula (M-1) and the formula (M-2) and the light emitting properties (particularly, external quantum efficiency) of the light emitting device is estimated as follows.

The present inventors have first noticed the fact that the compound (B) is a compound in which the difference between the maximum peak wavelength EB [nm] of the emission spectrum at 25° C. and the peak wavelength AB [nm] at the lowest energy side of the absorption spectrum at 25° C. is small. It was supposed that since the difference between EB and AB is small for the compound (B), the overlap between the emission spectrum and the absorption spectrum is large, self-absorption tends to occur, and the light emitting properties (particularly, external quantum efficiency) of the light emitting device lower due to the self-absorption. Then, the present inventors believed that if a compound (B) in which at least one of EB and AB is different is used together to suppress this self-absorption, the light emitting properties (particularly, external quantum efficiency) of the light emitting device are excellent. That is, it is guessed that if the compound (B1) and the compound (B2) satisfying at least one of the formula (M-1) and the formula (M-2) are used together in the composition for light emitting device of the present embodiment, the light emitting properties (particularly, external quantum efficiency) of the light emitting device become excellent.

Next, the present inventors investigated also designs (particularly, a design for more efficient electrical interaction) by which the compound (B1) and the compound (B2) more efficiently interact physically, chemically or electrically.

First, both the compound (B1) and the compound (B2) are compounds for which the half-value widths in the emission spectrum and the absorption spectrum are small.

Then, it was supposed that, for example, when the half-value width in the emission spectrum of the compound (B2) is small, the overlap between the emission spectrum of the compound (B2) and the absorption spectrum of the compound (B1) tends to be smaller. The present inventors believed that by increasing the overlap between the emission spectrum of the compound (B2) and the absorption spectrum of the compound (B1), a more efficient electrical interaction is obtained, and noticed the absolute value (hereinafter, referred to also as "|EB2-AB1|") of a difference between EB2 and AB1. More specifically, it was supposed that by regulating |EB2-AB1| to preferably 200 nm or less, for example, the overlap between the emission spectrum of the compound (B2) and the absorption spectrum of the compound (B1) increases, and resultantly, the light emitting properties (particularly, external quantum efficiency) of the light emitting device become excellent.

Further, it was supposed that, for example, when the half-value width in the emission spectrum of the compound (B1) is small, the overlap between the emission spectrum of the compound (B1) and the absorption spectrum of the compound (B2) tends to be smaller. The present inventors believed that a more efficient electrical interaction is obtained by increasing the overlap between the emission spectrum of the compound (B1) and the absorption spectrum of the compound (B2), and noticed the absolute value (hereinafter, referred to also as "|EB1-AB2|") of a difference between EB1 and AB2. More specifically, it was supposed that by regulating |EB1-AB2| to preferably 200 nm or less, for example, the overlap between the emission spectrum of the compound (B1) and the absorption spectrum of the compound (B2) increases, and resultantly, the light emitting properties (particularly, external quantum efficiency) of the light emitting device become excellent.

From the above-described standpoint, at least one of |EB2-AB1| and |EB1-AB2| is preferably 200 nm or less, more preferably 150 nm or less, further preferably 100 nm or less, particularly preferably 50 nm or less, especially preferably 30 nm or less, and especially more preferably 20 nm or less, since the light emitting device of the present embodiment is more excellent in external quantum efficiency. Meanwhile, at least one of |EB2-AB1| and |EB1-AB2| may be 0 nm or more, and it is preferably 1 nm or more, more preferably 2 nm or more, further preferably 3 nm or more, particularly preferably 5 nm or more, and especially preferably 10 nm or more, since the light emitting device of the present embodiment is more excellent in external quantum efficiency.

Further, |EB2-AB1| is preferably 200 nm or less, more preferably 150 nm or less, further preferably 100 nm or less, particularly preferably 50 nm or less, especially preferably 30 nm or less, and especially more preferably 20 nm or less, since the light emitting device of the present embodiment is more excellent in external quantum efficiency. Meanwhile, |EB2-AB1| may be 0 nm or more, and it is preferably 1 nm or more, more preferably 2 nm or more, further preferably 3 nm or more, particularly preferably 5 nm or more, and especially preferably 10 nm or more, since the light emitting device of the present embodiment is more excellent in external quantum efficiency.

Further, |EB1-AB2| is preferably 200 nm or less, more preferably 150 nm or less, further preferably 100 nm or less, particularly preferably 50 nm or less, especially preferably 30 nm or less, and especially more preferably 20 nm or less, since the light emitting device of the present embodiment is more excellent in external quantum efficiency. Meanwhile, |EB1-AB2| may be 0 nm or more, and it is preferably 1 nm or more, more preferably 2 nm or more, further preferably 3 nm or more, particularly preferably 5 nm or more, and especially preferably 10 nm or more, since the light emitting device of the present embodiment is more excellent in external quantum efficiency.

Further, both |EB2-AB1| and |EB1-AB2| are preferably 200 nm or less, more preferably 150 nm or less, further preferably 100 nm or less, particularly preferably 50 nm or less, especially preferably 30 nm or less, and especially more preferably 20 nm or less, since the light emitting device of the present embodiment is further excellent in external quantum efficiency. Meanwhile, both |EB2-AB1| and |EB1-AB2| may be 0 nm or more, and are preferably 1 nm or more, more preferably 2 nm or more, further preferably 3 nm or more, particularly preferably 5 nm or more, and especially preferably 10 nm or more, since the light emitting device of the present embodiment is further excellent in external quantum efficiency.

In the composition for light emitting device of the present embodiment, when the formula (M-1) is satisfied, EB2-EB1 is preferably 200 nm or less, more preferably 100 nm or less, further preferably 50 nm or less, particularly preferably 20 nm or less, and especially preferably 10 nm or less, since the light emitting device of the present embodiment is more excellent in external quantum efficiency. Further, in the composition for light emitting device of the present embodiment, when the formula (M-1) is satisfied, EB2-EB1 may be 0.1 nm or more, may be 0.5 nm or more, or may be 1 nm or more.

In the composition for light emitting device of the present embodiment, when the formula (M-2) is satisfied, AB2-AB1 is preferably 200 nm or less, more preferably 100 nm or less, further preferably 50 nm or less, particularly preferably 20 nm or less, and especially preferably 10 nm or less, since the light emitting device of the present embodiment is more excellent in external quantum efficiency. In the composition for light emitting device of the present embodiment, when the formula (M-2) is satisfied, AB2-AB1 is preferably 0.1 nm or more, more preferably 0.5 nm or more, and further preferably 1 nm or more, since the light emitting device of the present embodiment is more excellent in external quantum efficiency.

In the composition for light emitting device of the present embodiment, when the formula (M-1) is satisfied, it is preferable to satisfy AB1≤AB2, and it is more preferable to satisfy AB1<AB2, since the light emitting device of the present embodiment is more excellent in external quantum efficiency.

In the composition for light emitting device of the present embodiment, when the formula (M-2) is satisfied, it is preferable to satisfy EB1≤EB2, and EB1<EB2 may be satisfied, since the light emitting device of the present embodiment is more excellent in external quantum efficiency.

EB1 and EB2 are not particularly restricted, and for example, when the compound B1 and the compound B2 are used as a light emitting material, they are preferably in the visible region. In this case, EB1 and EB2 are preferably 380 nm or more, more preferably 400 nm or more, further preferably 420 nm or more, and particularly preferably 440 nm or more. EB1 and EB2 are preferably 750 nm or less, more preferably 620 nm or less, further preferably 570 nm or less, particularly preferably 495 nm or less, and especially preferably 480 nm or less.

AB1 and AB2 are not particularly restricted, and they are preferably 300 nm or more, more preferably 320 nm or more, further preferably 340 nm or more, particularly preferably 360 nm or more, especially preferably 380 nm or more, especially more preferably 400 nm or more, and especially further preferably 420 nm or more. Means while, AB1 and AB2 are preferably 750 nm or less, more preferably 620 nm or less, further preferably 570 nm or less, particularly preferably 495 nm or less, especially preferably 480 nm or less, especially more preferably 460 nm or less, ad especially further preferably 450 nm or less.

The maximum peak wavelength of the emission spectrum at room temperature of a compound can be evaluated by dissolving the compound in an organic solvent such as xylene, toluene, chloroform, tetrahydrofuran and the like to prepare a dilute solution ($1\times10^{-6}$% by mass to $1\times10^{-3}$% by mass), and measuring the PL spectrum of the dilute solution at room temperature. The organic solvent for dissolving the compound is preferably xylene.

The peak wavelength at the lowest energy side of the absorption spectrum at room temperature of a compound can be evaluated by dissolving the compound in an organic solvent such as xylene, toluene, chloroform, tetrahydrofuran and the like to prepare a dilute solution ($1\times10^{-6}$% by mass to $1\times10^{-3}$% by mass), and measuring the ultraviolet visible absorption spectrum of the dilute solution at room temperature. The organic solvent for dissolving the compound is preferably xylene.

[Compound (B)]

Next, the compound (B) will be described. Unless otherwise stated, the examples and preferable ranges and the like of the compound (B) described below are the same as the examples and preferable ranges and the like of the compound (B1) and the compound (B2).

The compound (B) is a compound having a condensed hetero ring skeleton (b) containing a boron atom and a nitrogen atom in the ring.

In the compound (B), at least one of nitrogen atoms contained in the condensed hetero ring skeleton (b) is preferably a nitrogen atom not forming a double bond, and all nitrogen atoms contained in the condensed hetero ring skeleton (b) are more preferably nitrogen atoms not forming a double bond.

The maximum peak wavelength (EB) of the emission spectrum at 25° C. of the compound (B) is not particularly restricted, and for example, when the compound (B) is used as a light emitting material, it is preferably in the visible region. In this case, EB is preferably 380 nm or more, more preferably 400 nm or more, further preferably 420 nm or more, and particularly preferably 440 nm or more. Meanwhile, EB is preferably 750 nm or less, more preferably 620 nm or less, further preferably 570 nm or less, particularly preferably 495 nm or less, and especially preferably 480 nm or less.

Further, when the compound (B) is used as a light emitting material, the half-value width of the maximum peak in the emission spectrum at 25° C. of the compound (B) is preferably 50 nm or less, more preferably 40 nm or less, further preferably 30 nm or less, and particularly preferably 25 nm or less.

The peak wavelength (AB) at the lowest energy side of the absorption spectrum at 25° C. of the compound (B) is not particularly restricted, and it is preferably 300 nm or more, more preferably 320 nm or more, further preferably 340 nm or more, particularly preferably 360 nm or more, especially preferably 380 nm or more, especially more preferably 400 nm or more, and especially further preferably 420 nm or more. Meanwhile, AB is preferably 750 nm or less, more preferably 620 nm or less, further preferably 570 nm or less, particularly preferably 495 nm or less, especially preferably 480 nm or less, especially more preferably 460 nm or less, and especially further preferably 450 nm or less.

Further, the half-value width of a peak at the lowest energy side of the absorption spectrum at 25° C. of the compound (B) is preferably 50 nm or less, more preferably 40 nm or less, and further preferably 30 nm or less.

The number of carbon atoms of the condensed hetero ring skeleton (b), not including the number of carbon atoms of the substituent, is usually 1 to 60, preferably 5 to 40, and more preferably 10 to 25.

The number of hetero atoms of the condensed hetero ring skeleton (b), not including the number of hetero atoms of the substituent, is usually 2 to 30, preferably 2 to 15, more preferably 2 to 10, further preferably 2 to 5, and particularly preferably 2 or 3.

The number of born atoms of the condensed hetero ring skeleton (b), not including the number of boron atoms of the substituent, is usually 1 to 10, preferably 1 to 5, more preferably 1 to 3, and further preferably 1.

The number of nitrogen atoms of the condensed hetero ring skeleton (b), not including the number of nitrogen atoms of the substituent, is usually 1 to 20, preferably 1 to 10, more preferably 1 to 5, further preferably 1 to 3, and particularly preferably 2.

The condensed hetero ring skeleton (b) is preferably a tri to dodecacyclic condensed hetero ring skeleton, more preferably a tri to hexacyclic condensed hetero ring skeleton, and further preferably a pentacyclic condensed hetero ring skeleton, since the light emitting device of the present embodiment is more excellent in external quantum efficiency.

The compound (B) can also be referred to as a compound having a hetero ring group (b') containing a condensed hetero ring skeleton (b).

The hetero ring group (b') may be a group obtained by removing from a polycyclic heterocyclic compound containing a boron atom and a nitrogen atom in the ring one or more hydrogen atoms bonding directly to atoms constituting the ring, and the group optionally has a substituent.

The substituent which the hetero ring group (b') optionally has is preferably a halogen atom, a cyano group, an alkyl group, a cycloalkyl group, an alkoxy group, a cycloalkoxy group, an aryl group, a monovalent hetero ring group or a substituted amino group, more preferably an alkyl group, a cycloalkyl group, an alkoxy group, a cycloalkoxy group, an aryl group, a monovalent hetero ring group or a substituted amino group, and further preferably an alkyl group, an aryl group or a substituted amino group, and these groups optionally further have a substituent.

The aryl group as the substituent which the hetero ring group (b') optionally has is preferably a group obtained by removing from a monocyclic or dicyclic to hexacyclic aromatic hydrocarbon one hydrogen atom bonding directly to an atom constituting the ring, more preferably a group obtained by removing from a monocyclic, dicyclic or tricyclic aromatic hydrocarbon one hydrogen atom bonding directly to an atom constituting the ring, further preferably a group obtained by removing from benzene, naphthalene, anthracene, phenanthrene or fluorene one hydrogen atom bonding directly to an atom constituting the ring, and particularly preferably a phenyl group, and these groups optionally have a substituent.

The monovalent hetero ring group as the substituent which the hetero ring group (b') optionally has is preferably a group obtained by removing from a monocyclic or dicyclic to hexacyclic heterocyclic compound one hydrogen atom bonding directly to an atom constituting the ring, more preferably a group obtained by removing from a monocyclic, dicyclic or tricyclic heterocyclic compound one hydrogen atom bonding directly to an atom constituting the ring, further preferably a group obtained by removing from pyridine, diazabenzene, triazine, azanaphthalene, diazanaphthalene, carbazole, dibenzofuran, dibenzothiophene, phenoxazine or phenothiazine one hydrogen atom bonding directly to an atom constituting the ring, and particularly preferably a group obtained by removing from pyridine, diazabenzene or triazine one hydrogen atom bonding directly to an atom constituting the ring, and these groups optionally have a substituent.

In the substituted amino group as the substituent which the hetero ring group (b') optionally has, the substituent which the amino group has is preferably an aryl group or a monovalent hetero ring group, and more preferably an aryl group, and these groups optionally further have a substituent. The examples and preferable ranges of the aryl group and the monovalent hetero ring group as the substituent which the amino group has are the same as the examples and preferable ranges of the aryl group and the monovalent hetero ring group as the substituent which the hetero ring group (b') optionally has, respectively.

The substituent which the substituent which the hetero ring group (b') optionally has optionally further has is preferably a halogen atom, an alkyl group, a cycloalkyl group, an alkoxy group, a cycloalkoxy group, an aryl group, a monovalent hetero ring group or a substituted amino group, more preferably an alkyl group, a cycloalkyl group, an aryl group, a monovalent hetero ring group or a substituted amino group, and further preferably an alkyl group or a cycloalkyl group, and these groups optionally further have a substituent, but it is preferable that they do not further have a substituent.

The examples and preferable ranges of the aryl group, the monovalent hetero ring group and the substituted amino group as the substituent which the substituent which the hetero ring group (b') optionally has optionally further has are the same as the examples and preferable ranges of the aryl group, the monovalent hetero ring group and the substituted amino group as the substituent which the hetero ring group (b') optionally has, respectively.

"The nitrogen atom not forming a double bond" means a nitrogen atom that is single-bonded to each of the other three atoms.

The phrase "containing a nitrogen atom not forming a double bond in the ring" means that a group represented by —N(—R$^N$)— (wherein, R$^N$ represents a hydrogen atom or a substituent) or the formula:

[Chemical Formula 6]

is contained in the ring.

The compound (B) is preferably a thermally activated delayed fluorescence (TADF) compound, since the light emitting device of the present embodiment is more excellent in external quantum efficiency.

$\Delta E_{ST}$ of the compound (B) may be 2.0 eV or less, may be 1.5 eV or less, may be 1.0 eV or less, may be 0.80 eV or less, or may be 0.60 eV or less, and it is preferably 0.50 eV or less, since the light emitting device of the present embodiment is more excellent in external quantum efficiency. Meanwhile, $\Delta E_{ST}$ of the compound (B) may be 0.001 eV or more, may be 0.01 eV or more, may be 0.10 eV or more, may be 0.20 eV or more, may be 0.30 eV or more, or may be 0.40 eV or more.

The compound (B) is preferably a low molecular weight compound.

The molecular weight of the compound (B) is preferably $1 \times 10^2$ to $5 \times 10^3$, more preferably $2 \times 10^2$ to $3 \times 10^3$, further preferably $3 \times 10^2$ to $1.5 \times 10^3$, and particularly preferably $4 \times 10^2$ to $1 \times 10^3$.

The compound (B) is preferably a compound represented by the formula (1-1) to the formula (1-3), more preferably a compound represented by the formula (1-2) or the formula (1-3), and further preferably a compound represented by the formula (1-2), since the light emitting device of the present embodiment is more excellent in external quantum efficiency.

At least one of the compound (B1) and the compound (B2) is preferably a compound represented by the formula (1-1), a compound represented by the formula (1-2) or a compound represented by the formula (1-3), more preferably a compound represented by the formula (1-2) or the formula (1-3), and further preferably a compound represented by the formula (1-2), since the light emitting device of the present embodiment is more excellent in external quantum efficiency.

Both the compound (B1) and the compound (B2) represent preferably a compound represented by the formula (1-1), a compound represented by the formula (1-2) or a compound represented by the formula (1-3), more preferably a compound represented by the formula (1-2) or the formula (1-3), and further preferably a compound represented by the formula (1-2), since the light emitting device of the present embodiment is further excellent in external quantum efficiency.

Ar$^1$, Ar$^2$ and Ar$^3$ are each preferably a group obtained by removing from a monocyclic, dicyclic or tricyclic aromatic hydrocarbon or a monocyclic, dicyclic or tricyclic heterocyclic compound one or more hydrogen atoms bonding directly to atoms constituting the ring, more preferably a group obtained by removing from a monocyclic aromatic hydrocarbon or a monocyclic heterocyclic compound one or more hydrogen atoms bonding directly to atoms constituting the ring, further preferably a group obtained by removing from benzene, pyridine or diazabenzene one or more hydrogen atoms bonding directly to atoms constituting the ring, and particularly preferably a group obtained by removing from benzene one or more hydrogen atoms bonding directly to atoms constituting the ring, since the light emitting device of the present embodiment is more excellent in external quantum efficiency, and these groups optionally have a substituent.

The examples and preferable ranges of the substituent which Ar$^1$, Ar$^2$ and Ar$^3$ optionally have are the same as the examples and preferable ranges of the substituent which the hetero ring group (b') optionally has.

Y$^2$ and Y$^3$ are each preferably a single bond, an oxygen atom, a sulfur atom, a group represented by —N(Ry)- or a methylene group, more preferably a single bond, an oxygen atom, a sulfur atom or a group represented by —N(Ry)-, further preferably an oxygen atom, a sulfur atom or a group represented by —N(Ry)-, and particularly preferably a group represented by —N(Ry)-, and these groups optionally have a substituent.

The examples and preferable ranges of the substituent which Y$^1$, Y$^2$ and Y$^3$ optionally have are the same as the examples and preferable ranges of the substituent which the hetero ring group (b') optionally has.

Ry is preferably an alkyl group, a cycloalkyl group, an aryl group or a monovalent hetero ring group, more preferably an aryl group or a monovalent hetero ring group, and further preferably an aryl group, and these groups optionally have a substituent.

The examples and preferable ranges of the aryl group and the monovalent hetero ring group represented by Ry are the same as the examples and preferable ranges of the aryl group and the monovalent hetero ring group as the substituent which the hetero ring group (b') optionally has, respectively.

The examples and preferable ranges of the substituent which Ry optionally has are the same as the examples and preferable ranges of the substituent which the hetero ring group (b') optionally has.

Ry may be bonded directly or via a connecting group to Ar$^1$, Ar$^2$ or Ar$^3$, but it is preferable that it is not bonded. The connecting group includes, for example, a group represented by —O—, a group represented by —S—, a group represented by —N(Ry)-, an alkylene group, a cycloalkylene group, an arylene group and a divalent hetero ring group, and is preferably a group represented by —O—, a group represented by —S—, a group represented by —N(Ry)- or a methylene group, and these groups optionally have a substituent.

As the compound (B), compounds represented by the following formulae and compounds B1 to B4 described later are exemplified.

[Chemical Formula 7]

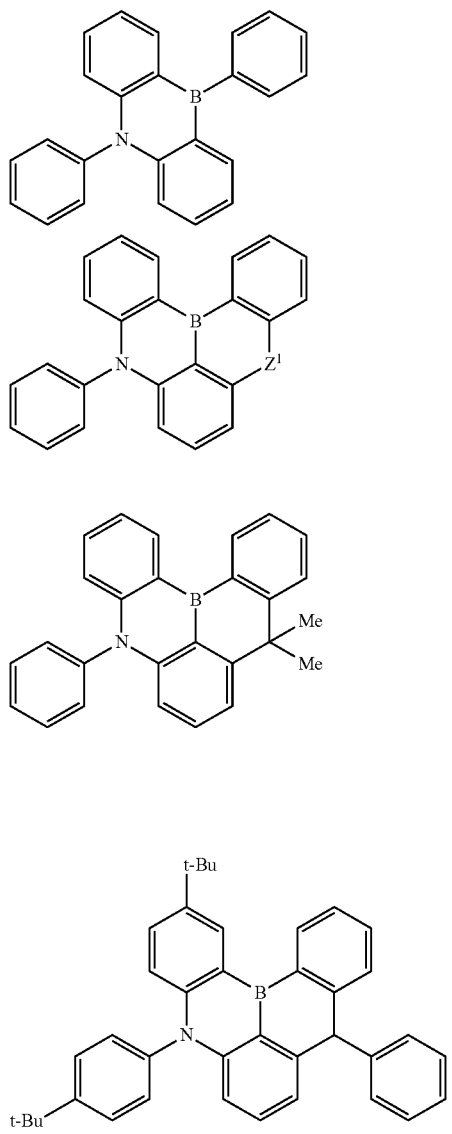

[Chemical Formula 8]

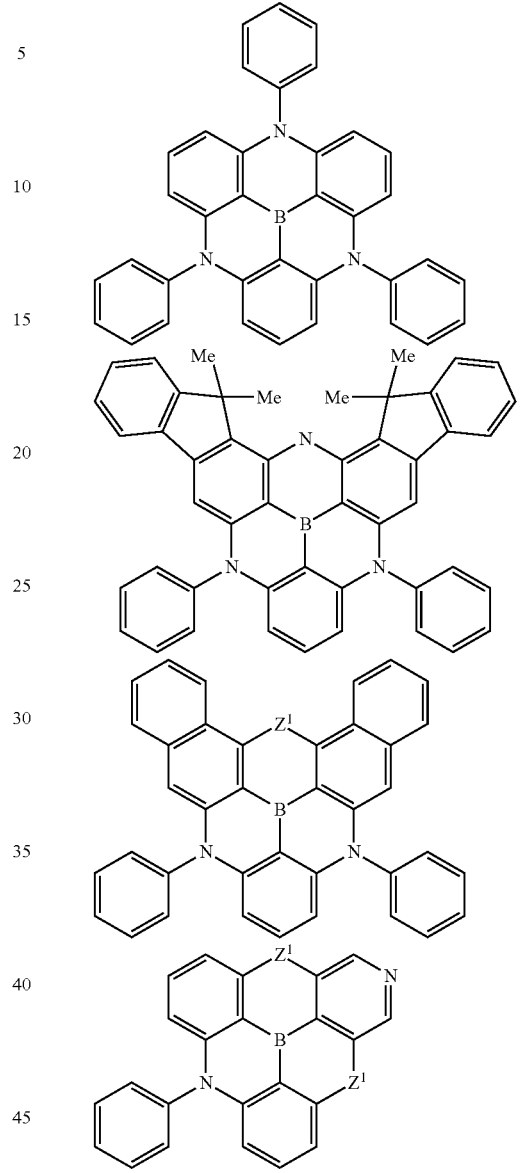

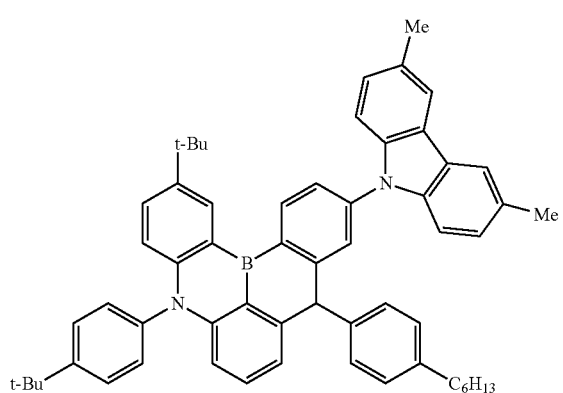

In the formulae, $Z^1$ represents an oxygen atom or a sulfur atom.

[Host Material]

It is preferable that the composition for light emitting device of the present embodiment further contains a host material having at least one function selected from hole injectability, hole transportability, electron injectability and electron transportability, since the light emitting device of the present embodiment is more excellent in external quantum efficiency. The composition for light emitting device of the present embodiment may contain the host material singly or in combination of two or more. However, the host material is different from the compound (B).

When the composition for light emitting device of the present embodiment further contains a host material, the host material and the compound (B) preferably interact physically, chemically or electrically. By this interaction, it becomes possible to improve or adjust, for example, the light emitting properties, the charge transportability or the charge injectability of the composition for light emitting device of the present embodiment.

When the composition for light emitting device of the present embodiment further contains a host material, if a light emitting material is explained as an example, the host material and the compound (B) interact electrically to transfer electrical energy efficiently from the host material to the compound (B), accordingly, the compound (B) can be allowed to emit light more efficiently, and the light emitting device of the present embodiment is more excellent in external quantum efficiency.

From the above-described standpoint, when the composition for light emitting device of the present embodiment further contains a host material, it is preferable that the lowest excited singlet state ($S_1$) of the host material is at the energy level higher than that of the lowest excited singlet state ($S_1$) of the compound (B), since the light emitting device of the present embodiment is more excellent in external quantum efficiency.

When the composition for light emitting device of the present embodiment further contains a host material, the host material and the compound (B) efficiently interact physically, chemically or electrically and the light emitting device of the present embodiment is more excellent in external quantum efficiency, hence, the absolute value (hereinafter, referred to also as "|EH-AB|") of a difference between EH (the maximum peak wavelength of the emission spectrum at 25° C. of the host material) and AB (the peak wavelength at the lowest energy side of the absorption spectrum at 25° C. of the compound (B)) is preferably 200 nm or less, more preferably 150 nm or less, further preferably 100 nm or less, particularly preferably 80 nm or less, especially preferably 60 nm or less, especially more preferably 30 nm or less, and especially further preferably 15 nm or less, since the light emitting device of the present embodiment is more excellent in external quantum efficiency. Meanwhile, |EH-AB| may be 0 nm or more, may be 1 nm or more, may be 2 nm or more, or 5 nm or more.

When the composition for light emitting device of the present embodiment further contains a host material, it is preferable that EH≤AB is satisfied, and it is more preferable that EH<AB is satisfied, since the light emitting device of the present embodiment is more excellent in external quantum efficiency.

EH is preferably 300 nm or more, and may be 320 nm or more, may be 340 nm or more, or may be 360 nm or more. Meanwhile, EH is preferably 750 nm or less, and may be 620 nm or less, may be 570 nm or less, may be 495 nm or less, may be 480 nm or less, or may be 460 nm or less.

Under the above-mentioned conditions, the relationship between |EH-AB| and the light emitting properties (particularly, external quantum efficiency) of the light emitting device is estimated as follows.

The present inventors investigated designs by which the host material and the compound (B) efficiently interact physically, chemically or electrically (particularly, a design for more efficient electrical interaction). First, it was guessed that the compound (B) is a compound in which the half-value width in the absorption spectrum is small, and by this, the half-value width in the absorption spectrum of the compound (B) is small. Under the conditions, it was guessed that if the half-value width in the absorption spectrum of the compound (B) is small, the overlap between the emission spectrum of the host material and the absorption spectrum of the compound (B) tends to be smaller. Under this state, the present inventors believed that an electrical interaction can be obtained more efficiently by increasing the overlap between the emission spectrum of the host material and the absorption spectrum of the compound (B), thus, focused on |EH-AB|. More specifically, it is presumed that by regulating |EH-AB| preferably to 200 nm or less, the overlap between the emission spectrum of the host material and the absorption spectrum of the compound (B) becomes large, thus, the electrical energy of the host material transfers quickly to the compound (B), and resultantly, the light emitting properties (particularly, external quantum efficiency) of the light emitting device are more excellent.

From the above standpoint, at least one of the absolute value (hereinafter, referred to also as |EH-AB1|) of a difference between EH and AB1 and the absolute value (hereinafter, referred to also as |EH-AB2|) of a difference between EH and AB2 is preferably 200 nm or less, more preferably 150 nm or less, further preferably 100 nm or less, particularly preferably 80 nm or less, especially preferably 60 nm or less, especially more preferably 30 nm or less, and especially further preferably 15 nm or less, since the light emitting device of the present embodiment is more excellent in external quantum efficiency. Meanwhile, at least one of |EH-AB1| and |EH-AB2| may be 0 nm or more, may be 1 nm or more, may be 2 nm or more, or may be 5 nm or more.

Further, |EH-AB1| is preferably 200 nm or less, more preferably 150 nm or less, further preferably 100 nm or less, particularly preferably 80 nm or less, especially preferably 60 nm or less, especially more preferably 30 nm or less, and especially further preferably 15 nm or less, since the light emitting device of the present embodiment is more excellent in external quantum efficiency. Meanwhile, |EH-AB1| may be 0 nm or more, may be 1 nm or more, may be 2 nm or more, or may be 5 nm or more.

Further, |EH-AB2| is preferably 200 nm or less, more preferably 150 nm or less, further preferably 100 nm or less, particularly preferably 80 nm or less, especially preferably 60 nm or less, especially more preferably 30 nm or less, and especially further preferably 15 nm or less, since the light emitting device of the present embodiment is more excellent in external quantum efficiency. Meanwhile, |EH-AB2| may be 0 nm or more, may be 1 nm or more, may be 2 nm or more, or may be 5 nm or more.

Further, both |EH-AB1| and |EH-AB2| are preferably 200 nm or less, more preferably 150 nm or less, further preferably 100 nm or less, particularly preferably 80 nm or less, especially preferably 60 nm or less, especially more preferably 30 nm or less, and especially further preferably 15 nm or less, since the light emitting device of the present embodiment is further excellent in external quantum efficiency. Meanwhile, both |EH-AB1| and |EH-AB2| may be 0 nm or more, may be 1 nm or more, may be 2 nm or more, or may be 5 nm or more.

When the composition for light emitting device of the present embodiment further contains a host material, it is preferable that EH≤AB1 is satisfied, and it is more preferable that EH<AB1 is satisfied, since the light emitting device of the present embodiment is more excellent in external quantum efficiency.

When the composition for light emitting device of the present embodiment further contains a host material, it is preferable that EH≤AB2 is satisfied, and it is more preferable that EH<AB2 is satisfied, since the light emitting device of the present embodiment is more excellent in external quantum efficiency.

When the composition for light emitting device of the present embodiment further contains a host material, it is preferable that EH≤AB1≤AB2 is satisfied, and it is more preferable that EH<AB1<AB2 is satisfied, since the light emitting device of the present embodiment is further excellent in external quantum efficiency.

When the composition for light emitting device of the present embodiment further contains a host material, the total content of the compounds (B) is usually 0.001 to 99 parts by mass, when the sum of the compounds (B) and the host material is taken as 100 parts by mass, and it is preferably 0.005 to 70 parts by mass, more preferably 0.01 to 50 parts by mass, further preferably 0.05 to 30 parts by mass, particularly preferably 0.1 to 10 parts by mass, and especially preferably 0.5 to 5 parts by mass, since the light emitting device of the present embodiment is more excellent in external quantum efficiency.

The host material is preferably one showing solubility in a solvent which is capable of dissolving the compound (B), since the light emitting device of the present embodiment can be fabricated by a wet method.

The host material is classified into low molecular weight compounds (low molecular weight host) and polymer compounds (polymer host), and the composition for light emitting device of the present embodiment may contain any host material. The host material which may be contained in the composition for light emitting device of the present embodiment is preferably a low molecular weight compound, since the light emitting device of the present embodiment is more excellent in external quantum efficiency.

The polymer host includes, for example, polymer compounds as a hole transporting material described later and polymer compounds as an electron transporting material described later.

The low molecular weight host is preferably a compound represented by the formula (H-1), since the light emitting device of the present embodiment is more excellent in external quantum efficiency. The compound represented by the formula (H-1) is preferably a compound having no condensed hetero ring skeleton (b) in the compound.

The molecular weight of the compound represented by the formula (H-1) is preferably $1\times10^2$ to $5\times10^3$, more preferably $2\times10^2$ to $3\times10^3$, further preferably $3\times10^2$ to $1.5\times10^3$, and particularly preferably $4\times10^2$ to $1\times10^3$.

The aryl group represented by $Ar^{H1}$ and $Ar^{H2}$ is preferably a group obtained by removing from a monocyclic or di to heptacyclic aromatic hydrocarbon one hydrogen atom bonding directly to an atom constituting the ring, more preferably a group obtained by removing from a monocyclic or di to pentacyclic aromatic hydrocarbon one hydrogen atom bonding directly to an atom constituting the ring, further preferably a group obtained by removing from benzene, naphthalene, anthracene, phenanthrene, dihydrophenanthrene, fluorene, benzoanthracene, benzophenanthrene, benzofluorene, pyrene, fluoranthene, perylene or benzofluoranthene one hydrogen atom bonding directly to an atom constituting the ring, and particularly preferably a group obtained by removing from benzene, naphthalene, anthracene, fluorene, pyrene or benzofluoranthene one hydrogen atom bonding directly to an atom constituting the ring, and these groups optionally have a substituent.

The arylene group represented by $L^{H1}$ is preferably a group obtained by removing from a monocyclic or di to heptacyclic aromatic hydrocarbon two hydrogen atoms bonding directly to atoms constituting the ring, more preferably a group obtained by removing from a monocyclic or di to pentacyclic aromatic hydrocarbon two hydrogen atoms bonding directly to atoms constituting the ring, further preferably a group obtained by removing from benzene, naphthalene, anthracene, phenanthrene, dihydrophenanthrene, fluorene, benzoanthracene, benzophenanthrene, benzofluorene, pyrene, fluoranthene, perylene or benzofluoranthene two hydrogen atoms bonding directly to atoms constituting the ring, and particularly preferably a group obtained by removing from benzene, naphthalene, anthracene, fluorene, pyrene or benzofluoranthene two hydrogen atoms bonding directly to atoms constituting the ring, and these groups optionally have a substituent.

The monovalent hetero ring group represented by $Ar^{H1}$ and $Ar^{H2}$ is preferably a group obtained by removing from a heterocyclic compound containing no condensed hetero ring skeleton (b) one hydrogen atom bonding directly to an atom constituting the ring, and this group optionally has a substituent. In the monovalent hetero ring group represented by $Ar^{H1}$ and $Ar^{H2}$, the heterocyclic compound containing no condensed hetero ring skeleton (b) includes heterocyclic compounds not containing a boron atom and a nitrogen atom in the ring among heterocyclic compounds explained in the section of the hetero ring group described above. The monovalent hetero ring group represented by $Ar^{H1}$ and $Ar^{H2}$ is preferably a group obtained by removing from a monocyclic or di to heptacyclic heterocyclic compound (preferably, a monocyclic or di to heptacyclic heterocyclic compound containing no condensed hetero ring skeleton (b)) one hydrogen atom bonding directly to an atom constituting the ring, more preferably a group obtained by removing from a monocyclic or di to pentacyclic heterocyclic compound (preferably, a monocyclic or di to pentacyclic heterocyclic compound containing no condensed hetero ring skeleton (b)) one hydrogen atom bonding directly to an atom constituting the ring, further preferably a group obtained by removing from pyridine, diazabenzene, triazine, azanaphthalene, diazanaphthalene, dibenzofuran, dibenzothiophene, carbazole, phenoxazine, phenothiazine, benzocarbazole, benzonaphthofuran, benzonaphthothiophene, dibenzocarbazole, indolocarbazole or indenocarbazole one hydrogen atom bonding directly to an atom constituting the ring, and particularly preferably a group obtained by removing from pyridine, diazabenzene, triazine, azanaphthalene, diazanaphthalene, dibenzofuran, dibenzothiophene, carbazole, benzocarbazole, benzonaphthofuran or benzonaphthothiophene one hydrogen atom bonding directly to an atom constituting the ring, and these groups optionally have a substituent.

The divalent hetero ring group represented by $L^{H1}$ is preferably a group obtained by removing from a heterocyclic compound containing no condensed hetero ring skeleton (b) two hydrogen atoms bonding directly to atoms constituting the ring. In the divalent hetero ring group represented by $L^{H1}$, the heterocyclic compound containing no condensed hetero ring skeleton (b) includes heterocyclic compounds not containing a boron atom and a nitrogen atom in the ring among heterocyclic compounds explained in the section of the hetero ring group described above. The divalent hetero ring group represented by $L^{H1}$ is preferably a group obtained by removing from a monocyclic or di to heptacyclic heterocyclic compound (preferably, a monocyclic or di to heptacyclic heterocyclic compound containing no condensed hetero ring skeleton (b)) two hydrogen atoms bonding directly to atoms constituting the ring, more preferably a group obtained by removing from a monocyclic or di to pentacyclic heterocyclic compound (preferably, a monocyclic or di to pentacyclic heterocyclic compound containing no condensed hetero ring skeleton (b)) two hydrogen atoms bonding directly to atoms constituting the ring, further preferably a group obtained by removing from pyridine, diazabenzene, triazine, azanaphthalene, diazanaphthalene, dibenzofuran, dibenzothiophene, carbazole, phenoxazine, phenothiazine, benzocarbazole, benzonaphthofuran, benzonaphthothiophene, dibenzocarbazole, indolocarbazole or indenocarbazole two hydrogen atoms bonding directly to atoms constituting the ring, and particularly preferably a group obtained by removing from pyridine, diazabenzene, triazine, azanaphthalene, diazanaphthalene, dibenzofuran, dibenzothiophene, carbazole, benzocarbazole, benzonaphthofuran or benzonaphthothiophene two hydrogen atoms bonding directly to atoms constituting the ring, and these groups optionally have a substituent.

In the substituted amino group represented by $Ar^{H1}$ and $Ar^{H2}$, the substituent which the amino group has is preferably an aryl group or a monovalent hetero ring group, and more preferably an aryl group, and these groups optionally further have a substituent. The examples and preferable ranges of the aryl group as the substituent which the amino group has are the same as the examples and preferable ranges of the aryl group represented by $Ar^{H1}$ and $Ar^{H2}$. The examples and preferable ranges of the monovalent hetero ring group as the substituent which the amino group has are the same as the examples and preferable ranges of the monovalent hetero ring group represented by $Ar^{H1}$ and $Ar^{H2}$.

It is preferable that at least one of $Ar^{H1}$ and $Ar^{H2}$ is an aryl group or a monovalent hetero ring group, and it is more preferable that both $Ar^{H1}$ and $Ar^{H2}$ are aryl groups or monovalent hetero ring groups, since the light emitting device of the present embodiment is more excellent in external quantum efficiency, and these groups optionally have a substituent.

The aryl group and the monovalent hetero ring group represented by $Ar^{H1}$ and $Ar^{H2}$ are each preferably a group obtained by removing from benzene, naphthalene, fluorene, pyridine, diazabenzene, triazine, azanaphthalene, diazanaphthalene, dibenzofuran, dibenzothiophene or carbazole one hydrogen atom bonding directly to an atom constituting the ring, more preferably a phenyl group, a naphthyl group, a fluorenyl group, a carbazolyl group, a dibenzothienyl group or a dibenzofuryl group, and further preferably a phenyl group, a naphthyl group or a carbazolyl group, since the light emitting device of the present embodiment is more excellent in external quantum efficiency, and these groups optionally have a substituent.

It is preferable that at least one of $L^{H1}$ is an arylene group or a divalent hetero ring group, and it is more preferable that all of $L^{H1}$ are arylene groups or divalent hetero ring groups, since the light emitting device of the present embodiment is more excellent in external quantum efficiency, and these groups optionally have a substituent.

The arylene group and the divalent hetero ring group represented by $L^{H1}$ are each preferably a group obtained by removing from benzene, naphthalene, anthracene, fluorene, pyrene, benzofluoranthene, pyridine, diazabenzene, triazine, azanaphthalene, diazanaphthalene, dibenzofuran, dibenzothiophene or carbazole two hydrogen atoms bonding directly to atoms (preferably, carbon atoms) constituting the ring, more preferably a group obtained by removing from benzene, naphthalene, anthracene, dibenzofuran, dibenzothiophene or carbazole two hydrogen atoms bonding directly to atoms (preferably, carbon atoms) constituting the ring, and further preferably a group obtained by removing from benzene, naphthalene, anthracene, dibenzofuran or dibenzothiophene two hydrogen atoms bonding directly to atoms constituting the ring, since the light emitting device of the present embodiment is more excellent in external quantum efficiency, and these groups optionally have a substituent.

The substituent which $Ar^{H1}$, $Ar^{H2}$ and $L^{H1}$ optionally have is preferably an alkyl group, a cycloalkyl group, an alkoxy group, a cycloalkoxy group, an aryl group, a monovalent hetero ring group, a substituted amino group, a cyano group or halogen atom, more preferably an alkyl group, a cycloalkyl group, an aryl group, a monovalent hetero ring group or a substituted amino group, and further preferably an alkyl group, an aryl group or a monovalent hetero ring group, and these groups optionally further have a substituent.

The examples and preferable ranges of the aryl group, the monovalent hetero ring group and the substituted amino group as the substituent which $Ar^{H1}$, $Ar^{H2}$ and $L^{H1}$ optionally have are the same as the examples and preferable ranges of the aryl group, the monovalent hetero ring group and the substituted amino group represented by $Ar^{H1}$ and $Ar^{H2}$, respectively.

The substituent which the substituent which $Ar^{H1}$, $Ar^{H2}$ and $L^{H1}$ optionally have optionally further has is preferably an alkyl group, a cycloalkyl group, an aryl group, a monovalent hetero ring group or a substituted amino group, and more preferably an alkyl group or a cycloalkyl group, and these groups optionally further have a substituent, but it is preferable that they do not further have a substituent.

The examples and preferable ranges of the aryl group, the monovalent hetero ring group and the substituted amino group as the substituent which the substituent which $Ar^{H1}$, $Ar^{H2}$ and $L^{H1}$ optionally have optionally further has are the same as the examples and preferable ranges of the aryl group, the monovalent hetero ring group and the substituted amino group represented by $Ar^{H1}$ and $Ar^{H2}$, respectively.

$n^{H1}$ is usually an integer of 0 or more and 10 or less, preferably an integer of 0 or more and 7 or less, more preferably an integer of 1 or more and 5 or less, further preferably an integer of 1 or more and 3 or less, and particularly preferably 1.

The compound represented by the formula (H-1) includes, for example, compounds represented by the following formulae and a compound H2 described later. In the formulae, $Z^1$ represents an oxygen atom or a sulfur atom. In the formulae, $Z^2$ represents a group represented by —CH= or a group represented by —N=.

[Chemical Formula 9]

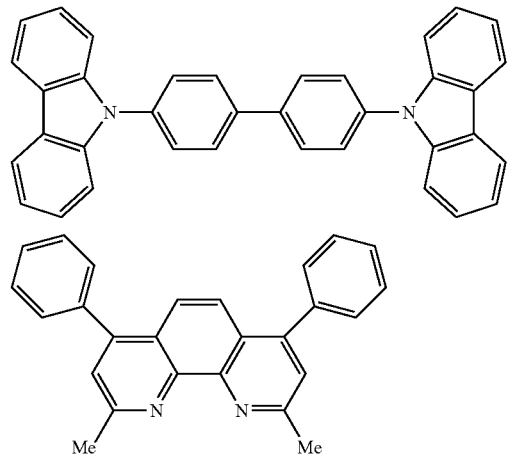

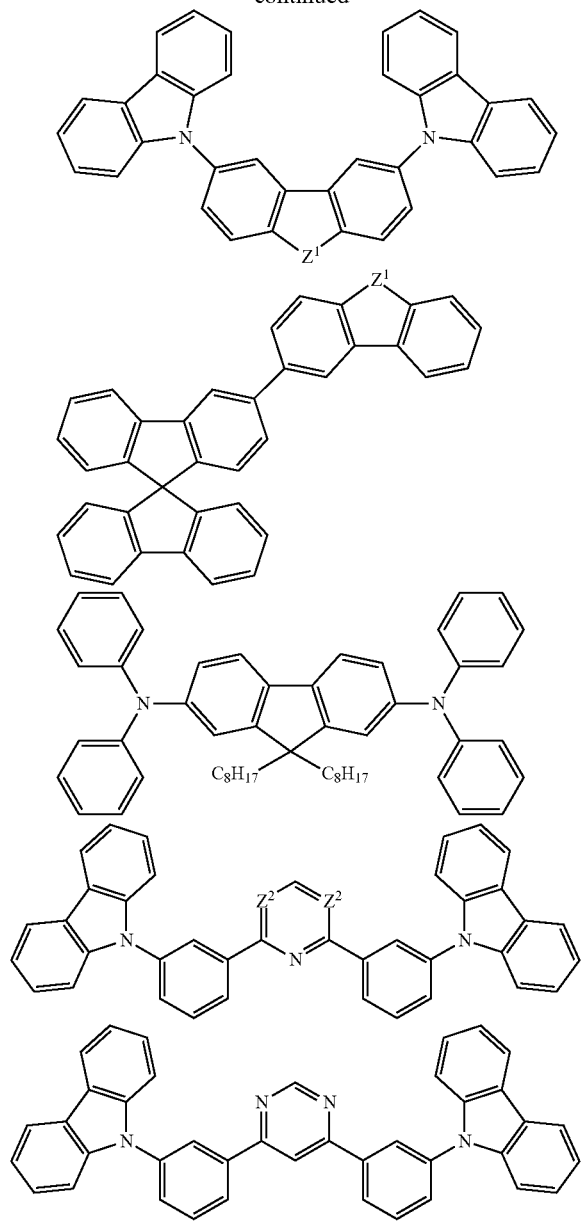
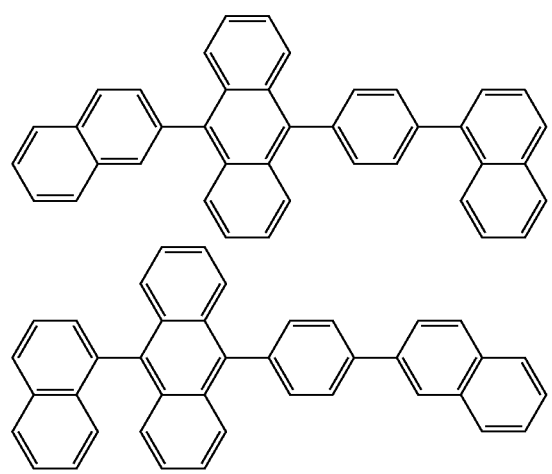
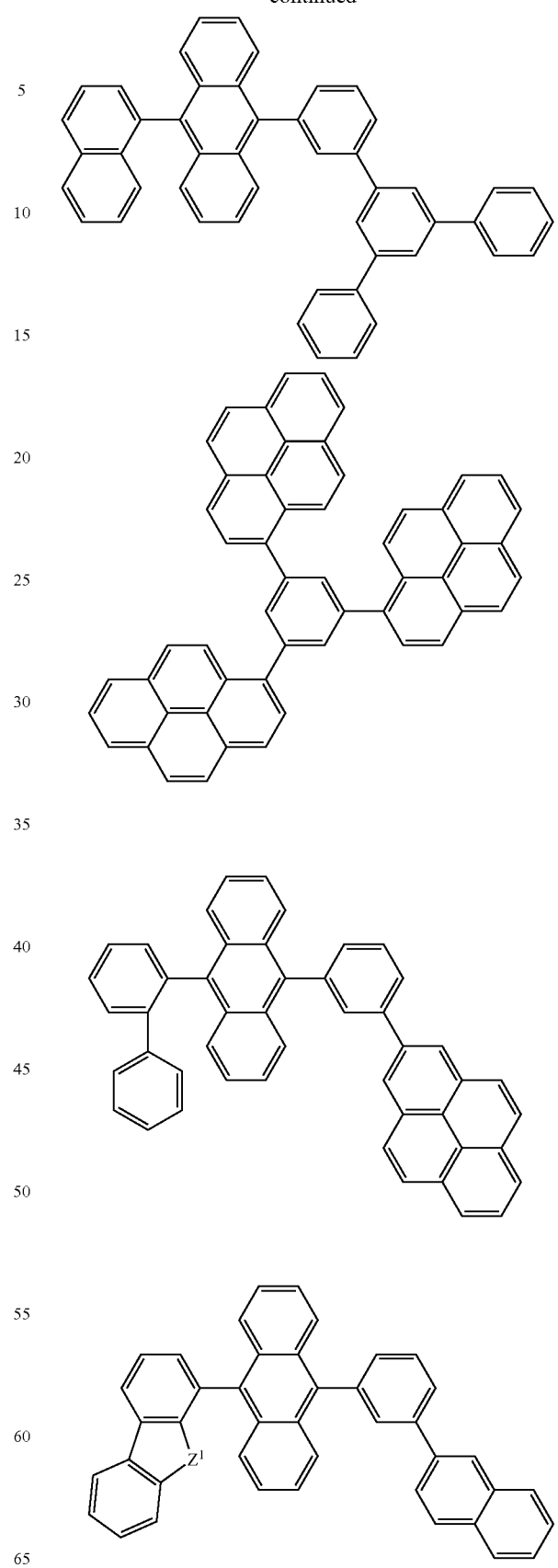
[Chemical Formula 10]

-continued

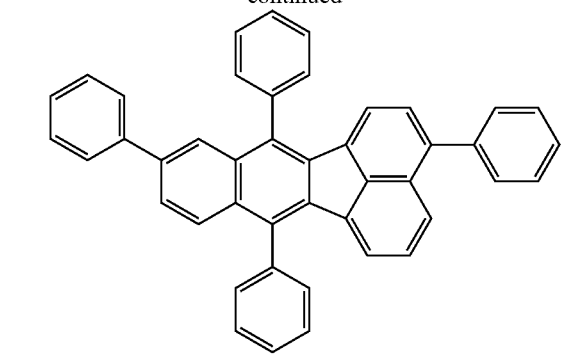

[Chemical Formula 11]

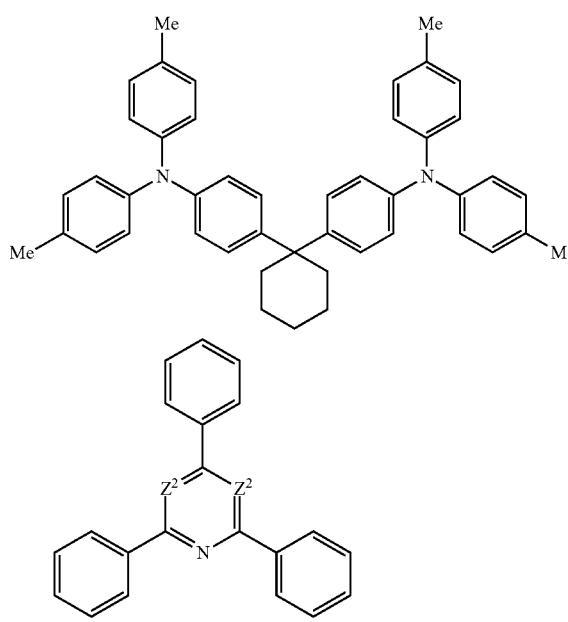

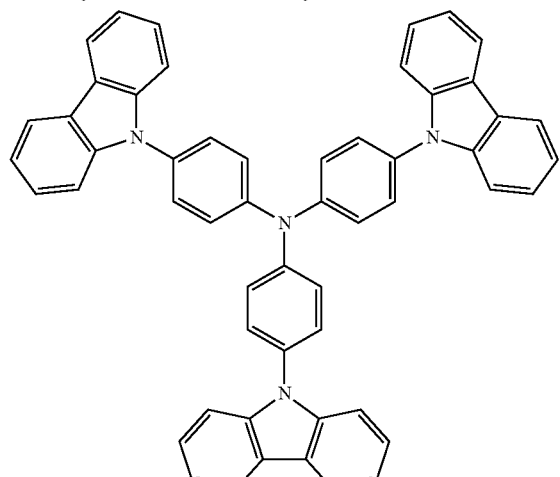

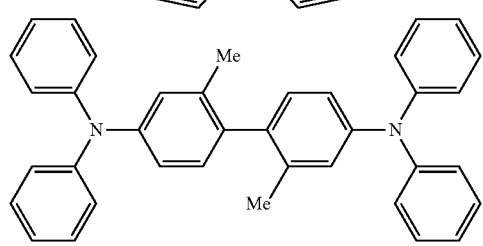

-continued

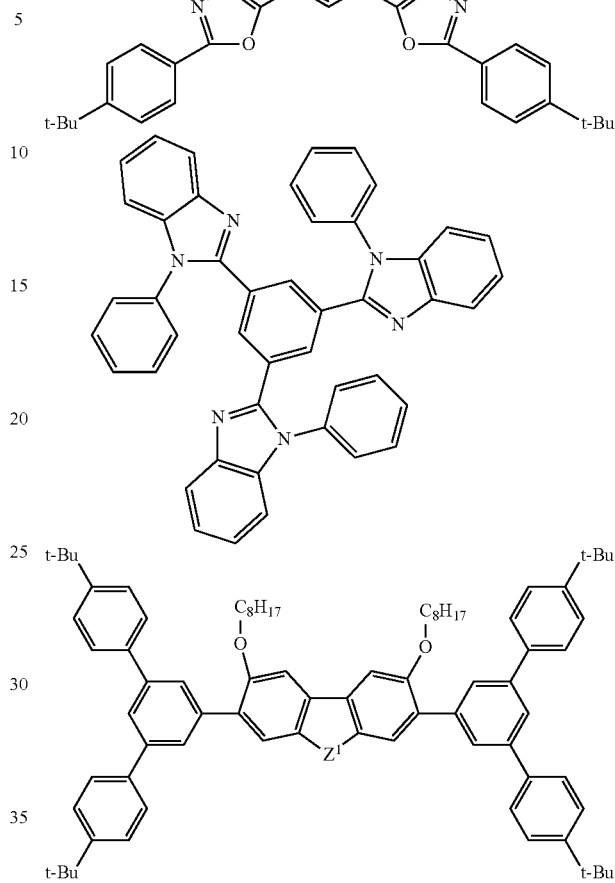

[Other Components]

The composition for light emitting device of the present embodiment may be a composition containing the compound (B), the above-described host material, and at least one selected from the group consisting of a hole transporting material, a hole injection material, an electron transporting material, an electron injection material, a light emitting material, an antioxidant and a solvent. The hole transporting material, the hole injection material, the electron transporting material, the electron injection material and the light emitting material are different from the compound (B).

[Ink]

The composition containing the compound (B) and a solvent (hereinafter, referred to as "ink") is suitable for fabricating a light emitting device using a wet method such as, for example, a spin coat method, a casting method, a microgravure coat method, a gravure coat method, a bar coat method, a roll coat method, a wire bar coat method, a dip coat method, a spray coat method, a screen printing method, a flexo printing method, an offset printing method, an inkjet printing method, a capillary coat method, a nozzle coat method and the like. The viscosity of the ink may be adjusted according to the type of the printing method, and is preferably 1 mPa·s to 20 mPa·s at 25° C.

The solvent contained in the ink is preferably a solvent capable of dissolving or uniformly dispersing solid components in the ink. The solvent includes, for example, chlorine-based solvents, ether-based solvents, aromatic hydrocarbon-based solvents, aliphatic hydrocarbon-based solvents, ketone-based solvents, ester-based solvents, polyhydric alcohol-based solvents, alcohol-based solvents, sulfoxide-based solvents and amide-based solvents.

In the ink, the compounding amount of the solvent is usually 1000 parts by mass to 10000000 parts by mass, when the sum of the compounds (B) is taken as 100 parts by mass.

The solvent may be used singly or in combination of two or more.

Hole Transporting Material

The hole transporting material is classified into low molecular weight compounds and polymer compounds, and polymer compounds having a cross-linkable group are preferable.

The polymer compound includes, for example, polyvinylcarbazole and derivatives thereof; and polyarylenes having an aromatic amine structure in the side chain or main chain, and derivatives thereof. The polymer compound may be a compound to which an electron accepting site such as fullerene, tetrafluorotetracyanoquinodimethane, tetracyanoethylene, trinitrofluorenone and the like is bonded.

In the composition for light emitting device of the present embodiment, when a hole transporting material is contained, the compounding amount of the hole transporting material is usually 1 part by mass to 10000 parts by mass, when the sum of the compounds (B) is taken as 100 parts by mass.

The hole transporting material may be used singly or in combination of two or more.

Electron Transporting Material

The electron transporting material is classified into low molecular weight compounds and polymer compounds. The electron transporting material may have a cross-linkable group.

The low molecular weight compound includes, for example, a metal complex having 8-hydroxyquinoline as a ligand, oxadiazole, anthraquinodimethane, benzoquinone, naphthoquinone, anthraquinone, tetracyanoanthraquinodimethane, fluorenone, diphenyldicyanoethylene and diphenoquinone, and derivatives thereof.

The polymer compound includes, for example, polyphenylene, polyfluorene, and derivatives thereof. The polymer compound may be doped with a metal.

In the composition for light emitting device of the present embodiment, when an electron transporting material is contained, the compounding amount of the electron transporting material is usually 1 part by mass to 10000 parts by mass, when the sum of the compounds (B) is taken as 100 parts by mass.

The electron transporting material may be used singly or in combination of two or more.

Hole Injection Material and Electron Injection Material

The hole injection material and the electron injection material are each classified into low molecular weight compounds and polymer compounds. The hole injection material and the electron injection material may have a cross-linkable group.

The low molecular weight compound includes, for example, metal phthalocyanines such as copper phthalocyanine and the like; carbon; oxides of metals such as molybdenum, tungsten and the like; metal fluorides such as lithium fluoride, sodium fluoride, cesium fluoride, potassium fluoride and the like.

The polymer compound includes electrically conductive polymers such as, for example, polyaniline, polythiophene, polypyrrole, polyphenylenevinylene, polythienylenevinylene, polyquinoline and polyquinoxaline, and derivatives thereof; a polymer containing an aromatic amine structure in the main chain or side chain, and the like.

In the composition for light emitting device of the present embodiment, when a hole injection material and/or an electron injection material is contained, the compounding amounts of the hole injection material and the electron injection material are each usually 1 part by mass to 10000 parts by mass, when the sum of the compounds (B) is taken as 100 parts by mass.

The hole injection material and the electron injection material each may be used singly or in combination of two or more.

Ion Doping

When the hole injection material or the electron injection material contains an electrically conductive polymer, the electric conductivity of the electrically conductive polymer is preferably $1 \times 10^{-5}$ S/cm to $1 \times 10^{3}$ S/cm. For adjusting the electric conductivity of the electrically conductive polymer within such a range, the electrically conductive polymer can be doped with an appropriate amount of ions. The kind of the ion to be doped is an anion for the hole injection material and a cation for the electron injection material. The anion includes, for example, a polystyrenesulfonic ion, an alkylbenzenesulfonic ion and a camphorsulfonic ion. The cation includes, for example, a lithium ion, a sodium ion, a potassium ion and a tetrabutylammonium ion.

The ion to be doped may be used singly or in combination of two or more.

Light Emitting Material

The light emitting material is classified into low molecular weight compounds and polymer compounds. The light emitting material may have a cross-linkable group.

The low molecular weight compound includes, for example, naphthalene and derivatives thereof, anthracene and derivatives thereof, perylene and derivatives thereof, and triplet light emitting complexes having iridium, platinum or europium as the central metal.

The polymer compound includes polymer compounds containing, for example, an arylene group such as a phenylene group, a naphthalenediyl group, a fluorenediyl group, a phenanthrenediyl group, a dihydrophenanthrenediyl group, an anthracenediyl group, a pyrenediyl group and the like; an aromatic amine residue such as a group obtained by removing from an aromatic amine two hydrogen atoms, and the like; and a divalent hetero ring group such as a carbazolediyl group, a phenoxazinediyl group, a phenothiazinediyl group and the like.

In the composition for light emitting device of the present embodiment, when a light emitting material is contained, the content of the light emitting material is usually 1 part by mass to 10000 parts by mass, when the sum of the compounds (B) is taken as 100 parts by mass.

The light emitting material may be used singly or in combination of two or more.

Antioxidant

The antioxidant may be a compound which is soluble in the same solvent as for the compound (B) and does not inhibit light emission and charge transportation, and includes, for example, phenol type antioxidants and phosphorus-based antioxidants.

In the composition for light emitting device of the present embodiment, when an antioxidant is contained, the compounding amount of the antioxidant is usually 0.00001 parts by mass to 10 parts by mass, when the sum of the compounds (B) is taken as 100 parts by mass. The antioxidant may be used singly or in combination of two or more.

<Film>

The film of the present embodiment contains the composition for light emitting device described above. The film of the present embodiment is suitable as a light emitting layer in a light emitting device. The film of the present embodiment can be fabricated, for example, by a wet method using an ink. Further, the film of the present embodiment can be fabricated, for example, by a dry method such as a vacuum vapor deposition method and the like. The method for fabricating the film of the present embodiment by a dry method includes, for example, a method of vapor-depositing the above-described composition for light emitting device and a method of co-vapor-depositing each of two or more compounds (B).

The thickness of the film is usually 1 nm to 10 μm.

<Light Emitting Device>

The light emitting device of the present embodiment contains the composition for light emitting device described above.

The light emitting device of the present embodiment may be one having, for example, an anode, a cathode, and an organic layer disposed between the anode and the cathode and containing the composition for light emitting device described above.

[Layer Constitution]

The layer containing the composition for light emitting device of the present embodiment is usually one or more layers selected from the group consisting of a light emitting layer, a hole transporting layer, a hole injection layer, an electron transporting layer and an electron injection layer, and preferably is a light emitting layer. These layers contain a light emitting material, a hole transporting material, a hole injection material, an electron transporting material and an electron injection material, respectively. These layers can be formed by the same method as for the fabrication of the film described above using a light emitting material, a hole transporting material, a hole injection material, an electron transporting material and an electron injection material, respectively.

The light emitting device has a light emitting layer between an anode and a cathode. The light emitting device of the present embodiment preferably has at least one of a hole injection layer and a hole transporting layer between an anode and a light emitting layer, from the standpoint of hole injectability and hole transportability, and preferably has at least one of an electron injection layer and an electron transporting layer between a cathode and a light emitting layer, from the standpoint of electron injectability and electron transportability.

The materials of a hole transporting layer, an electron transporting layer, a light emitting layer, a hole injection layer and an electron injection layer include the hole transporting material, the electron transporting material, the light emitting material, the hole injection material and the electron injection material and the like described above, respectively, in addition to the composition for light emitting device of the present embodiment.

When the material of a hole transporting layer, the material of an electron transporting layer and the material of a light emitting layer are soluble in a solvent used in forming layers adjacent to the hole transporting layer, the electron transporting layer and the light emitting layer, respectively, in fabricating a light emitting device, it is preferable that the material has a cross-linkable group for avoiding the material from being dissolved in the solvent. After forming each layer using the material having a cross-linkable group, the cross-linkable group can be cross-linked to insolubilize the layer.

The method for forming each layer such as a light emitting layer, a hole transporting layer, an electron transporting layer, a hole injection layer, an electron injection layer and the like in the light emitting device of the present invention includes, for example, dry methods such as a method of vacuum vapor-deposition from a powder and the like and wet methods such as a method by film formation from a solution or melted state and the like when a low molecular weight compound is used, and includes, for example, wet methods such as a method by film formation from a solution or melted state and the like when a polymer compound is used. The order, number and thickness of layers to be laminated are adjusted in consideration of, for example, light emission efficiency, driving voltage and luminance life.

[Substrate/Electrode]

The substrate of a light emitting device may be a substrate on which an electrode can be formed and which does not chemically change in forming an organic layer, and it is, for example, a substrate made of a material such as glass, plastic, silicon and the like. In the case of an opaque substrate, it is preferable that the electrode farthest from the substrate is transparent or semi-transparent.

The material of the anode includes, for example, electrically conductive metal oxides and semi-transparent metals, preferably includes indium oxide, zinc oxide, tin oxide; electrically conductive compounds such as indium-tin-oxide (ITO), indium-zinc-oxide and the like; argentine-palladium-copper (APC) complex; NESA, gold, platinum, silver and copper.

The material of the cathode includes, for example, metals such as lithium, sodium, potassium, rubidium, cesium, beryllium, magnesium, calcium, strontium, barium, aluminum, zinc, indium and the like; alloys composed of two or more of them; alloys composed of one or more of them and one or more of silver, copper, manganese, titanium, cobalt, nickel, tungsten and tin; and graphite and graphite intercalation compounds. The alloy includes, for example, a magnesium-silver alloy, a magnesium-indium alloy, a magnesium-aluminum alloy, an indium-silver alloy, a lithium-aluminum alloy, a lithium-magnesium alloy, a lithium-indium alloy and a calcium-aluminum alloy.

The anode and the cathode each may take a laminated structure composed of two or more layers.

[Application]

The light emitting device of the present embodiment can be suitably used as a light source for backlight of a liquid crystal display device, a light source for illumination, organic EL illumination, a display device of computers, televisions, portable terminals and the like (for example, organic EL display and organic EL television).

Suitable embodiments of the present invention have been explained above, but the present invention is not limited to them.

For example, one aspect of the present invention may relate to the method for producing a composition for light emitting device described above.

In one embodiment, the method for producing a composition for light emitting device may be a production method comprising a preparation step of preparing a compound (B1) having a condensed hetero ring skeleton (b1) containing a boron atom and a nitrogen atom in the ring, a sorting step of sorting a compound (B2) having a condensed hetero ring skeleton (b2) containing a boron atom and a nitrogen atom in the ring and in which the maximum peak wavelength of the emission spectrum at 25° C. is larger than the maximum peak wavelength of the emission spectrum at 25° C. of the compound (B1) and/or the peak wavelength at the lowest energy side of the absorption spectrum at 25° C. is smaller than the peak wavelength at the lowest energy side of the absorption spectrum at 25° C. of the compound (B1), and a production step of mixing the compound (B1) prepared in the preparation step and the compound (B2) sorted in the sorting step to obtain a composition for light emitting device (hereinafter, referred to also as "production method (1)").

The production method (1) (preferably, the sorting step in the production method (1)) may further include a step of determining the maximum peak wavelength (EB2) of the emission spectrum at 25° C. of the compound (B2) and/or the peak wavelength (AB2) at the lowest energy side of the absorption spectrum at 25° C. of the compound (B2). Further, the production method (1) (preferably, the sorting step in the production method (1)) may further include a step of determining the maximum peak wavelength (EB1) of the emission spectrum at 25° C. of the compound (B1) and/or the peak wavelength (AB1) at the lowest energy side of the absorption spectrum at 25° C. of the compound (B1).

In the sorting step in the production method (1), the compound (B2) may be further sorted so that |EB2-AB1| is 200 nm or less.

In the sorting step in the production method (1), the compound (B2) may be further sorted so that (EB1-AB2| is 200 nm or less.

In the production method (1), the half-value width of the maximum peak of the emission spectrum at 25° C. of the compound (B1) is preferably 50 nm or less. That is, in the preparation step in the production method (1), it is preferable to prepare the compound (B1) in which the half-value width of the maximum peak of the emission spectrum at 25° C. is 50 nm or less.

In the production method (1), the half-value width of the maximum peak of the emission spectrum at 25° C. of the compound (B2) is preferably 50 nm or less. That is, in the sorting step in the production method (1), it is preferable to sort the compound (B2) in which the half-value width of the maximum peak of the emission spectrum at 25° C. is 50 nm or less.

In the production method (1), the half-value width of a peak at the lowest energy side of the absorption spectrum at 25° C. of the compound (B1) is preferably 50 nm or less. That is, in the preparation step in the production method (1), it is preferable to prepare the compound (B1) in which the half-value width of a peak at the lowest energy side of the absorption spectrum at 25° C. is 50 nm or less.

In the production method (1), the half-value width of a peak at the lowest energy side of the absorption spectrum at 25° C. of the compound (B2) is preferably 50 nm or less. That is, in the sorting step in the production method (1), it is preferable to sort the compound (B2) in which the half-value width of a peak at the lowest energy side of the absorption spectrum at 25° C. is 50 nm or less.

In another embodiment, the method for producing a composition for light emitting device may be a production method comprising a preparation step of preparing a compound (B2) having a condensed hetero ring skeleton (b2) containing a boron atom and a nitrogen atom in the ring, a sorting step of sorting a compound (B1) having a condensed hetero ring skeleton (b1) containing a boron atom and a nitrogen atom in the ring and in which the maximum peak wavelength of the emission spectrum at 25° C. is smaller than the maximum peak wavelength of the emission spectrum at 25° C. of the compound (B2) and/or the peak wavelength at the lowest energy side of the absorption spectrum at 25° C. is larger than the peak wavelength at the lowest energy side of the absorption spectrum at 25° C. of the compound (B2), and a production step of mixing the compound (B2) prepared in the preparation step and the compound (B1) sorted in the sorting step to obtain a composition for light emitting device (hereinafter, referred to also as "production method (2)").

The production method (2) (preferably, the sorting step in the production method (2)) may include a step of determining the maximum peak wavelength (EB1) of the emission spectrum at 25° C. of the compound (B1) and/or the peak wavelength (AB1) at the lowest energy side of the absorption spectrum at 25° C. of the compound (B1). Further, the production method (2) (preferably, the sorting step in the production method (2)) may further include a step of determining the maximum peak wavelength (EB2) of the emission spectrum at 25° C. of the compound (B2) and/or the peak wavelength (AB2) at the lowest energy side of the absorption spectrum at 25° C. of the compound (B2).

In the sorting step in the production method (2), the compound (B1) may be further sorted so that |EB2-AB1| is 200 nm or less.

In the sorting step in the production method (2), the compound (B1) may be further sorted so that |EB1-AB2| is 200 nm or less.

In the production method (2), the half-value width of the maximum peak of the emission spectrum at 25° C. of the compound (B2) is preferably 50 nm or less. That is, in the preparation step in the production method (2), it is preferable to prepare the compound (B2) in which the half-value width of the maximum peak of the emission spectrum at 25° C. is 50 nm or less.

In the production method (2), the half-value width of the maximum peak of the emission spectrum at 25° C. of the compound (B1) is preferably 50 nm or less. That is, in the sorting step of the production method (2), it is preferable to sort the compound (B1) in which the half-value width of the maximum peak of the emission spectrum at 25° C. is 50 nm or less.

In the production method (2), the half-value width of a peak at the lowest energy side of the absorption spectrum at 25° C. of the compound (B2) is preferably 50 nm or less. That is, in the preparation step in the production method (2), it is preferable to prepare the compound (B2) in which the half-value width of a peak at the lowest energy side of the absorption spectrum at 25° C. is 50 nm or less.

In the production method (2), the half-value width of a peak at the lowest energy side of the absorption spectrum at 25° C. of the compound (B1) is preferably 50 nm or less. That is, in the sorting step of the production method (2), it is preferable to sort the compound (B2) in which the half-value width of a peak at the lowest energy side of the absorption spectrum at 25° C. is 50 nm or less.

In the production steps in the production method (1) and the production method (2), the method of mixing the compound (B1) and the compound (B2) is not particularly restricted. The mixing method includes, for example, a method of dissolving the compound (B1) and the compound (B2) in the solvent explained in the section of the ink described above and mixing them, a method of mixing the compound (B1) and the compound (B2) in solid state, a method of mixing the compound (B1) and the compound (B2) by co-vapor-deposition, and the like.

Still another aspect of the present invention may relate to the method for producing a light emitting device described above.

In one embodiment, the method for producing a light emitting device may be a method for producing a light emitting device containing an anode, a cathode, and an organic layer disposed between the anode and the cathode, and this production method has a step of producing a composition for light emitting device by the above-described production method (for example, the production method (1) or the production method (2)) and a step of forming an organic layer using the composition for light emitting device produced in the above step.

In this embodiment, the organic layer can be formed, for example, using the same method as for the fabrication of a film described above. Further, in the light emitting device production method of the present embodiment, the production method explained in the section of <Light emitting device> described above may be used. Further, the light emitting device obtained by the light emitting device production method of the present embodiment includes, for example, light emitting devices explained in the section of <Light emitting device> described above.

EXAMPLES

The present invention will be illustrated further in detail by examples below, by the present invention is not limited to these examples.

For calculation of the value of $\Delta E_{ST}$ of a compound, the ground state of the compound was structurally optimized by density-functional approach at B3LYP level, and in this procedure, 6-31G* was used as the basis function. Using Gaussian09 as the quantum chemistry calculation program, $\Delta E_{ST}$ of the compound was calculated by time-dependent density-functional approach at B3LYP level.

In examples, the maximum peak wavelength of the emission spectrum of a compound at room temperature was measured by a spectrophotometer (manufactured by JASCO Corporation, FP-6500) at room temperature. A compound was dissolved in xylene at a concentration of about $8 \times 10^{-4}\%$ by mass and the resultant xylene solution was used as a specimen. As the excitation light, ultraviolet (UV) light having a wavelength of 325 nm was used.

In examples, the peak wavelength at the lowest energy side of the absorption spectrum at room temperature of the compound was measured by a UV Vis spectrophotometer (manufactured by Varian, Cary 5E) at room temperature. A compound was dissolved in xylene at a concentration of about $8 \times 10^{-4}\%$ by mass and the resultant xylene solution was used as a specimen.

<Acquisition and Synthesis of Compounds H1, H2 and B1 to B4>

A compound H1 manufactured by Luminescence Technology Corp. was used. The maximum peak wavelength (EH) of the emission spectrum at room temperature of the compound H1 was 373 nm.

A compound H2 was synthesized with reference to a method described in International Publication WO2011/098030. The maximum peak wavelength (EH) of the emission spectrum at room temperature of the compound H2 was 430 nm.

A compound B1 was synthesized with reference to a method described in International Publication WO2015/102118. The maximum peak wavelength (EB) of the emission spectrum at room temperature of the compound B1 was 453 nm. The half-value width of the maximum peak of the emission spectrum at room temperature of the compound B1 was 22 nm. The peak wavelength (AB) at the lowest energy side of the absorption spectrum at room temperature of the compound B1 was 441 nm. The half-value width of a peak at the lowest energy side of the absorption spectrum at room temperature of the compound B1 was 22 nm. $\Delta E_{ST}$ of the compound B1 was 0.457 eV.

A compound B2 manufactured by Luminescence Technology Corp. was used. The maximum peak wavelength (EB) of the emission spectrum at room temperature of the compound B2 was 452 nm. The half-value width of the maximum peak of the emission spectrum at room temperature of the compound B2 was 22 nm. The peak wavelength (AB) at the lowest energy side of the absorption spectrum at room temperature of the compound B2 was 439 nm. The half-value width of a peak at the lowest energy side of the absorption spectrum at room temperature of the compound B2 was 26 nm. $\Delta E_{ST}$ of the compound B2 was 0.494 eV.

A compound B3 was synthesized with reference to a method described in International Publication WO2015/102118. The maximum peak wavelength (EB) of the emission spectrum at room temperature of the compound B3 was 452 nm. The half-value width of the maximum peak of the emission spectrum at room temperature of the compound B3 was 22 nm. The peak wavelength (AB) at the lowest energy side of the absorption spectrum at room temperature of the compound B3 was 438 nm. The half-value width of a peak at the lowest energy side of the absorption spectrum at room temperature of the compound B3 was 22 nm. $\Delta E_{ST}$ of the compound B3 was 0.447 eV.

A compound B4 was synthesized with reference to a method described in International Publication WO2015/102118. The maximum peak wavelength (EB) of the emission spectrum at room temperature of the compound B4 was 453 nm. The half-value width of the maximum peak of the emission spectrum at room temperature of the compound B4 was 21 nm. The peak wavelength (AB) at the lowest energy side of the absorption spectrum at room temperature of the compound B4 was 439 nm. The half-value width of a peak at the lowest energy side of the absorption spectrum at room temperature of the compound B4 was 28 nm. $\Delta E_{ST}$ of the compound B4 was 0.479 eV.

[Chemical Formula 12]

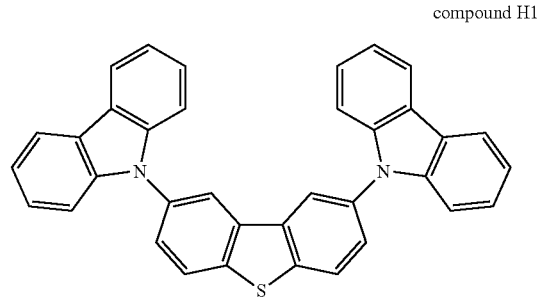

compound H1 compound H2

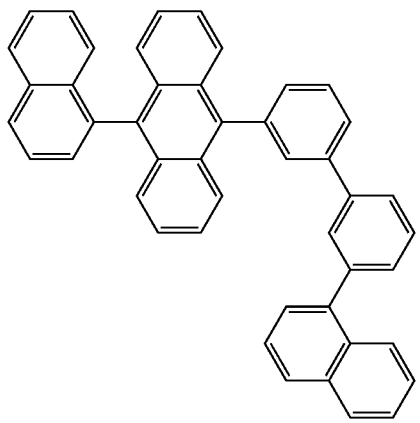

[Chemical Formula 13]

compound B1

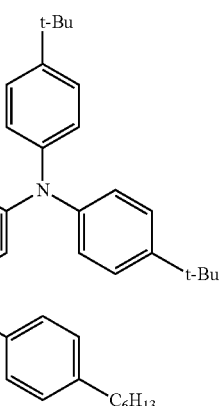

compound B2

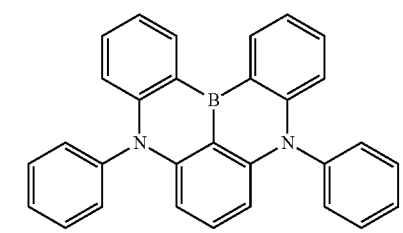

compound B3

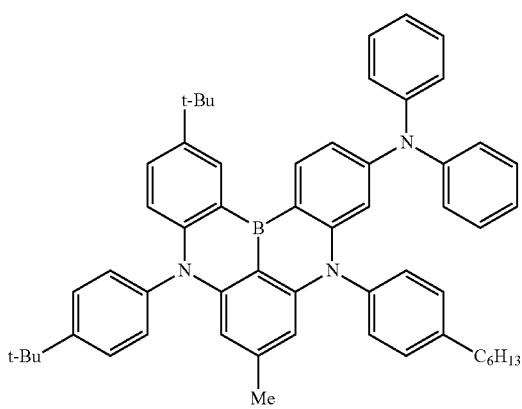

compound B4

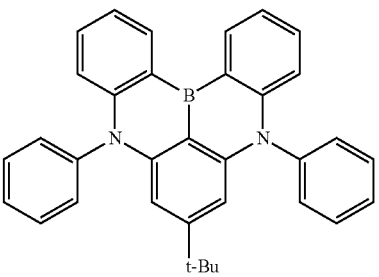

<Example D1> Fabrication and Evaluation of Light Emitting Device D1

(Formation of Anode and Hole Injection Layer)

An ITO film was attached with a thickness of 45 nm to a glass substrate by a sputtering method, to form an anode. On the anode, a hole injection material ND-3202 (manufactured by Nissan Chemical Corp.) was spin-coated, to form a film with a thickness of 35 nm. The substrate carrying the hole injection layer laminated thereon was heated on a hot plate at 50° C. for 3 minutes, and further heated at 230° C. for 15 minutes, under an air atmosphere, to form a hole injection layer.

(Formation of Hole Transporting Layer)

The polymer compound HTL-1 was dissolved in xylene at a concentration of 0.7% by mass. The resultant xylene solution was spin-coated on the hole injection layer, to form a film with a thickness of 20 nm, and the film was heated on a hot plate at 180° C. for 60 minutes under a nitrogen gas atmosphere, to form a hole transporting layer. The polymer compound HTL-1 is a polymer compound of Polymer Example 1 in International Publication WO2014/102543.

(Formation of Light Emitting Layer)

The compound H1, the compound B3 and the compound B2 (compound H1/compound B3/compound B2=99% by mass/0.5% by mass/0.5% by mass) were dissolved at a concentration of 2% by mass in toluene. The resultant toluene solution was spin-coated on the hole transporting layer, to form a film with a thickness of 60 nm, and the film was heated at 130° C. for 10 minutes under a nitrogen gas atmosphere, to form a light emitting layer.

(Formation of Cathode)

The substrate carrying the light emitting layer formed thereon was placed in a vapor deposition machine and the internal pressure thereof was reduced to $1.0 \times 10^{-4}$ Pa or less, then, as the cathode, sodium fluoride was vapor-deposited with a thickness of about 4 nm on the light emitting layer, then, aluminum was vapor-deposited with a thickness of about 80 nm on the sodium fluoride layer. After vapor deposition, the substrate carrying the cathode formed thereon was sealed with a glass substrate, to fabricate a light emitting device D1.

(Evaluation of Light Emitting Device)

Voltage was applied to the light emitting device D1, to observe EL light emission. The external quantum efficiency [%] at 0.1 mA/cm² was measured.

Examples D2 to D4 and Comparative Examples CD1 to CD2

Fabrication and evaluation of light emitting devices D2 to D4 and CD1 to CD2

Light emitting devices D2 to D4 and CD1 to CD2 were fabricated in the same manner as in Example D1, except that materials and composition ratios (% by mass) described in Table 1 were used instead of "the compound H1, the compound B3 and the compound B2 (compound H1/compound B3/compound B2=99% by mass/0.5$ by mass/0.5% by mass)" in (Formation of light emitting layer) of Example D1.

Voltage was applied to the light emitting devices D2 to D4 and CD1 to CD2, to observe EL light emission. The external quantum efficiency [%] at 0.1 mA/cm² was measured.

The results of Examples D1 to D4 and Comparative Examples CD1 to CD2 are shown in Table 1. The relative values of the external quantum efficiency of the light emitting devices D1 to D4 and CD2, when the external quantum efficiency of the light emitting device CD1 is taken as 1.0, are shown.

TABLE 1

| | Light emitting device | material | Light emitting layer Composition ratio (% by mass) | EH (nm) | EB1 (nm) | AB1 (nm) | EB2 (nm) | AB2 (nm) | External quantum efficiency (relative value) |
|---|---|---|---|---|---|---|---|---|---|
| Example D1 | D1 | H1/B3/B2 | 99/0.5/0.5 | 373 | 452 | 438 | 452 | 439 | 1.9 |
| Example D2 | D2 | H1/B3/B1 | 99/0.5/0.5 | 373 | 452 | 438 | 453 | 441 | 1.8 |
| Example D3 | D3 | H1/B2/B1 | 99/0.5/0.5 | 373 | 452 | 439 | 453 | 441 | 1.9 |
| Example D4 | D4 | H1/B2/B5 | 99/0.5/0.5 | 373 | 452 | 439 | 453 | 439 | 1.4 |
| Comparative Example CD1 | CD1 | H1/B1 | 99/1 | 373 | 453 | 441 | — | — | 1.0 |
| Comparative Example CD2 | CD2 | H1/B2 | 99/1 | 373 | 452 | 439 | — | — | 1.0 |

Examples D5 to D8 and Comparative Example CD3

Fabrication and Evaluation of Light Emitting Devices D5 to D8 and CD3

Light emitting devices D5 to D8 and CD3 were fabricated in the same manner as in Example D1, except that materials and composition ratios (% by mass) described in Table 2 were used instead of "the compound H1, the compound B3 and the compound B2 (compound H1/compound B3/compound B2=99% by mass/0.5% by mass/0.5% by mass)" in (Formation of light emitting layer) of Example D1.

Voltage was applied to the light emitting devices D5 to D8 and CD3, to observe EL light emission. The external quantum efficiency [%] at 0.1 mA/cm² was measured.

The results of Examples D5 to D8 and Comparative Example CD3 are shown in Table 2. The relative values of the external quantum efficiency of the light emitting devices D5 to D8, when the external quantum efficiency of the light emitting device CD3 is taken as 1.0, are shown.

TABLE 2

| | Light emitting device | material | Light emitting layer Composition ratio (% by mass) | EH (nm) | EB1 (nm) | AB1 (nm) | EB2 (nm) | AB2 (nm) | External quantum efficiency (relative value) |
|---|---|---|---|---|---|---|---|---|---|
| Example D5 | D5 | H2/B3/B2 | 99/0.5/0.5 | 430 | 452 | 438 | 452 | 439 | 4.4 |
| Example D6 | D6 | H2/B3/B1 | 99/0.5/0.5 | 430 | 452 | 438 | 453 | 441 | 4.3 |

TABLE 2-continued

|  | Light emitting device | material | Light emitting layer Composition ratio (% by mass) | EH (nm) | EB1 (nm) | AB1 (nm) | EB2 (nm) | AB2 (nm) | External quantum efficiency (relative value) |
|---|---|---|---|---|---|---|---|---|---|
| Example D7 | D7 | H2/B2/B1 | 99/0.5/0.5 | 430 | 452 | 439 | 453 | 441 | 4.2 |
| Example D8 | D8 | H2/B2/B4 | 99/0.5/0.5 | 430 | 452 | 439 | 453 | 439 | 2.7 |
| Comparative Example CD3 | CD3 | H2/B2 | 99/1 | 430 | 452 | 439 | — | — | 1.0 |

INDUSTRIAL APPLICABILITY

The composition of the present invention is useful for producing a light emitting device excellent in external quantum efficiency.

The invention claimed is:

1. A light emitting device comprising
an anode,
a cathode, and
an organic layer disposed between said anode and said cathode and containing a composition for light emitting device,
wherein
said composition for light emitting device contains two or more compounds (B) having a condensed hetero ring skeleton (b) containing a boron atom and a nitrogen atom in the ring, and
said compound (B) contains a compound (B1) and a compound (B2) satisfying at least one of the formula (M-1) and the formula (M-2):

EB1<EB2    (M-1)

AB1<AB2    (M-2)

wherein, EB1 represents the maximum peak wavelength [nm] of the emission spectrum at 25° C. of the compound (B1), EB2 represents the maximum peak wavelength [nm] of the emission spectrum at 25° C. of the compound (B2), AB1 represents the peak wavelength [nm] at the lowest energy side of the absorption spectrum at 25° C. of the compound (B1), and AB2 represents the peak wavelength [nm] at the lowest energy side of the absorption spectrum at 25° C. of the compound (B2).

2. The light emitting device according to claim 1, wherein at least one of said compound (B1) and said compound (B2) is a compound represented by the formula (1-1), a compound represented by the formula (1-2) or a compound represented by the formula (1-3):

[Chemical Formula 1]

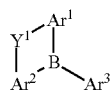

(1-1)

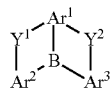

(1-2)

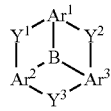

(1-3)

wherein,
$Ar^1$, $Ar^2$ and $Ar^3$ each independently represent an aromatic hydrocarbon group or a hetero ring group, and these groups optionally have a substituent, when a plurality of the substituents are present, they may be the same or different and may be combined together to form a ring together with atoms to which they are attached,
$Y^1$ represents a group represented by —N(Ry)-,
$Y^2$ and $Y^3$ each independently represent a single bond, an oxygen atom, a sulfur atom, a selenium atom, a group represented by —N(Ry)-, an alkylene group or a cycloalkylene group, and these groups optionally have a substituent, when a plurality of the substituents are present, they may be the same or different and may be combined together to form a ring together with atoms to which they are attached, Ry represents a hydrogen atom, an alkyl group, a cycloalkyl group, an aryl group or a monovalent hetero ring group, and these groups optionally have a substituent, when a plurality of the substituents are present, they may be the same or different and may be combined together to form a ring together with atoms to which they are attached, when a plurality of Ry are present, they may be the same or different, Ry may be bonded directly or via a connecting group to $Ar^1$, $Ar^2$ or $Ar^3$.

3. The light emitting device according to claim 2, wherein both said compound (B1) and said compound (B2) represent said compound represented by the formula (1-1), said compound represented by the formula (1-2) or said compound represented by the formula (1-3).

4. The light emitting device according to claim 2, wherein at least one of said compound (B1) and said compound (B2) is said compound represented by the formula (1-2).

5. The light emitting device according to claim 4, wherein both said compound (B1) and said compound (B2) represent said compound represented by the formula (1-2).

6. The light emitting device according to claim 2, wherein said $Y^2$ and said $Y^3$ are groups represented by —N(Ry)-.

7. The light emitting device according to claim 1, wherein said compound (B1) and said compound (B2) satisfy said formula (M-2).

8. The light emitting device according to claim 1, wherein at least one of the absolute value of a difference between said EB1 and said AB2 and the absolute value of a difference between said EB2 and said AB1 is 200 nm or less.

9. The light emitting device according to claim 1, wherein the absolute value of a difference between the energy level of the lowest triplet excited state and the energy level of the lowest singlet excited state of said compound (B1) is 0.50 eV or less, and
the absolute value of a difference between the energy level of the lowest triplet excited state and the energy level of the lowest singlet excited state of said compound (B2) is 0.50 eV or less.

10. The light emitting device according to claim 1, wherein said composition for light emitting device further contains a host material.

11. The light emitting device according to claim 10, wherein said host material contains a compound represented by the formula (H-1):

[Chemical Formula 2]

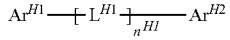
(H-1)

wherein, $Ar^{H1}$ and $Ar^{H2}$ each independently represent an aryl group, a monovalent hetero ring group or a substituted amino group, and these groups optionally have a substituent, when a plurality of the substituents are present, they may be the same or different and may be combined together to form a ring together with atoms to which they are attached, $n^{H1}$ represents an integer of 0 or more, $L^{H1}$ represents an arylene group, a divalent hetero ring group, an alkylene group or a cycloalkylene group, and these groups optionally have a substituent, when a plurality of the substituents are present, they may be the same or different and may be combined together to form a ring together with atoms to which they are attached, when a plurality of $L^{H1}$ are present, they may be the same or different.

12. The light emitting device according to claim 10, wherein the difference between the maximum peak wavelength EH [nm] of the emission spectrum at 25° C. of said host material and at least one of said AB1 and said AB2 is 200 nm or less.

13. The light emitting device according to claim 1, wherein said composition for light emitting device further contains at least one selected from the group consisting of a hole transporting material, a hole injection material, an electron transporting material, an electron injection material, a light emitting material, an antioxidant and a solvent.

14. A composition for light emitting device comprising two or more compounds (B) having a condensed hetero ring skeleton (b) containing a boron atom and a nitrogen atom in the ring, wherein said compound (B) contains a compound (B1) and a compound (B2) satisfying at least one of the formula (M-1) and the formula (M-2):

EB1<EB2 (M-1)

AB1<AB2 (M-2)

wherein, EB1 represents the maximum peak wavelength [nm] of the emission spectrum at 25° C. of the compound (B1), EB2 represents the maximum peak wavelength [nm] of the emission spectrum at 25° C. of the compound (B2), AB1 represents the peak wavelength [nm] at the lowest energy side of the absorption spectrum at 25° C. of the compound (B1), and AB2 represents the peak wavelength [nm] at the lowest energy side of the absorption spectrum at 25° C. of the compound (B2).

15. The composition for light emitting device according to claim 14, further comprising a host material.

16. The composition for light emitting device according to claim 15, wherein said host material contains a compound represented by the formula (H-1):

[Chemical Formula 3]

(H-1)

wherein, $Ar^{H1}$ and $Ar^{H2}$ each independently represent an aryl group, a monovalent hetero ring group or a substituted amino group, and these groups optionally have a substituent, when a plurality of the substituents are present, they may be the same or different and may be combined together to form a ring together with atoms to which they are attached, $n^{H1}$ represents an integer of 0 or more, $L^{H1}$ represents an arylene group, a divalent hetero ring group, an alkylene group or a cycloalkylene group, and these groups optionally have a substituent, when a plurality of the substituents are present, they may be the same or different and may be combined together to form a ring together with atoms to which they are attached, when a plurality of $L^{H1}$ are present, they may be the same or different.

17. The composition for light emitting device according to claim 15, wherein the difference between the maximum peak wavelength EH [nm] of the emission spectrum at 25° C. of said host material and at least one of said AB1 and said AB2 is 200 nm or less.

18. The composition for light emitting device according to claim 14, further comprising at least one selected from the group consisting of a hole transporting material, a hole injection material, an electron transporting material, an electron injection material, a light emitting material, an antioxidant and a solvent.

19. A method for producing a composition for light emitting device, comprising a preparation step of preparing a compound (B1) having a condensed hetero ring skeleton (b1) containing a boron atom and a nitrogen atom in the ring, a sorting step of sorting a compound (B2) having a condensed hetero ring skeleton (b2) containing a boron atom and a nitrogen atom in the ring and in which the maximum peak wavelength of the emission spectrum at 25° C. is larger than the maximum peak wavelength of the emission spectrum at 25° C. of said compound (B1) and/or the peak wavelength at the lowest energy side of the absorption spectrum at 25° C. is smaller than the peak wavelength at the lowest energy side of the absorption spectrum at 25° C. of said compound (B1), and a production step of mixing the compound (B1) prepared in said preparation step and the compound (B2) sorted in said sorting step to obtain a composition for light emitting device.

20. The production method according to claim 19, wherein said sorting step includes a step of determining the maximum peak wavelength of the emission spectrum at 25° C. of said compound (B2) and/or the peak wavelength at the lowest energy side of the absorption spectrum at 25° C. of said compound (B2).

21. A method for producing a composition for light emitting device, comprising
- a preparation step of preparing a compound (B2) having a condensed hetero ring skeleton (b2) containing a boron atom and a nitrogen atom in the ring,
- a sorting step of sorting a compound (B1) having a condensed hetero ring skeleton (b1) containing a boron atom and a nitrogen atom in the ring and in which the maximum peak wavelength of the emission spectrum at 25° C. is smaller than the maximum peak wavelength of the emission spectrum at 25° C. of said compound (B2) and/or the peak wavelength at the lowest energy side of the absorption spectrum at 25° C. is larger than the peak wavelength at the lowest energy side of the absorption spectrum at 25° C. of said compound (B2), and
- a production step of mixing the compound (B2) prepared in said preparation step and the compound (B1) sorted in said sorting step to obtain a composition for light emitting device.

22. The production method according to claim 21, wherein said sorting step includes a step of determining the maximum peak wavelength of the emission spectrum at 25° C. of said compound (B1) and/or the peak wavelength at the lowest energy side of the absorption spectrum at 25° C. of said compound (B1).

23. A method for producing a light emitting device having an anode, a cathode, and an organic layer disposed between said anode and said cathode, comprising
- a step of producing a composition for light emitting device by the production method as described in claim 19, and
- a step of forming said organic layer using said composition for light emitting device produced in the above step.

* * * * *